United States Patent
Fischer et al.

(10) Patent No.: US 8,980,886 B2
(45) Date of Patent: Mar. 17, 2015

(54) ANTHRANILIC ACID DERIVATIVES

(75) Inventors: Rüdiger Fischer, Pulheim (DE); Christoph Grondal, Köln (DE); Markus Heil, Leichlingen (DE); Heinz-Juergen Wroblowsky, Langenfeld (DE); Ernst Rudolf Gesing, Erkrath (DE); Arnd Voerste, Köln (DE); Ulrich Görgens, Ratingen (DE)

(73) Assignee: Bayer Cropscience AG, Monheim (DE)

( * ) Notice: Subject to any disclaimer, the term of this patent is extended or adjusted under 35 U.S.C. 154(b) by 319 days.

(21) Appl. No.: 13/160,281

(22) Filed: Jun. 14, 2011

(65) Prior Publication Data

US 2011/0312953 A1 Dec. 22, 2011

Related U.S. Application Data

(60) Provisional application No. 61/354,895, filed on Jun. 15, 2010.

(30) Foreign Application Priority Data

Jun. 15, 2010 (EP) .................................... 10166062

(51) Int. Cl.
| | | |
|---|---|---|
| A61K 31/535 | (2006.01) | |
| C07D 239/42 | (2006.01) | |
| A61K 31/42 | (2006.01) | |
| A61K 31/44 | (2006.01) | |
| C07D 239/02 | (2006.01) | |
| C07D 207/30 | (2006.01) | |
| C07D 277/20 | (2006.01) | |
| C07D 249/04 | (2006.01) | |
| C07D 249/08 | (2006.01) | |
| C07D 263/02 | (2006.01) | |
| C07D 403/06 | (2006.01) | |
| A01N 43/56 | (2006.01) | |
| A01N 43/713 | (2006.01) | |
| A01N 43/76 | (2006.01) | |
| A01N 43/78 | (2006.01) | |
| C07D 401/06 | (2006.01) | |
| C07D 413/06 | (2006.01) | |
| C07D 417/06 | (2006.01) | |

(52) U.S. Cl.
CPC .............. *C07D 403/06* (2013.01); *A01N 43/56* (2013.01); *A01N 43/713* (2013.01); *A01N 43/76* (2013.01); *A01N 43/78* (2013.01); *C07D 401/06* (2013.01); *C07D 413/06* (2013.01); *C07D 417/06* (2013.01)
USPC ........ 514/230.5; 514/256; 514/374; 514/343; 544/242; 548/560; 548/202; 548/255; 548/262.2; 548/215

(58) Field of Classification Search
USPC ............... 514/230.5, 256, 374, 343; 544/242; 548/560, 202, 255, 262.2, 215
See application file for complete search history.

(56) References Cited

U.S. PATENT DOCUMENTS

| | | | |
|---|---|---|---|
| 5,705,476 | A | 1/1998 | Hoffarth |
| 6,344,193 | B1* | 2/2002 | Hammock et al. ........... 424/93.2 |
| 6,602,823 | B1 | 8/2003 | Roechling et al. |
| 8,101,550 | B2* | 1/2012 | Alig et al. ..................... 504/100 |
| 2007/0129407 | A1 | 6/2007 | Koyanagi et al. |
| 2008/0221168 | A1 | 9/2008 | Schmidt et al. |
| 2009/0149506 | A1 | 6/2009 | Funke et al. |
| 2010/0029478 | A1* | 2/2010 | Alig et al. ..................... 504/100 |
| 2010/0048578 | A1 | 2/2010 | Jachman et al. |
| 2010/0048640 | A1 | 2/2010 | Jachmann et al. |
| 2010/0113794 | A1 | 5/2010 | Nokura et al. |

FOREIGN PATENT DOCUMENTS

| | | |
|---|---|---|
| EP | 0 681 865 | 11/1995 |
| EP | 1 911 751 | 4/2008 |
| WO | 98/35553 | 8/1998 |
| WO | 00/35278 | 6/2000 |
| WO | 0170671 | 9/2001 |
| WO | 03015518 | 2/2003 |
| WO | 03015519 | 2/2003 |
| WO | 03016282 | 2/2003 |
| WO | 03016283 | 2/2003 |
| WO | 03016284 | 2/2003 |

(Continued)

OTHER PUBLICATIONS

Zhang et al.; "Synthesis and Preliminary Biological Evaluation of Novel Pyrazolo[1,5-a] Pyrazin-4(5H)-One Derivatives as Potential Agents Against A549 Lung Cancer Cells"; Bioorganic & Medicinal Chemistry 16; 2008; pp. 10165-10171.

(Continued)

*Primary Examiner* — James O Wilson
*Assistant Examiner* — Oluwafemi Masha
(74) *Attorney, Agent, or Firm* — Miles & Stockbridge PC

(57) ABSTRACT

The present invention relates to novel anthranilic acid derivatives of the general formula (I)

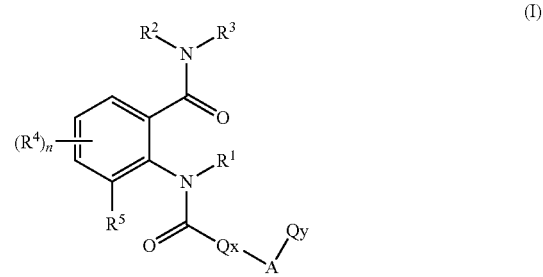

in which $R^1$, $R^2$, $R^3$, $R^4$, $R^5$, Qx, A, Qy and n have the meanings given in the description, to their use as insecticides and acaricides for controlling animal pests, also in combination with other agents for activity boosting, and to a plurality of processes for their preparation.

10 Claims, No Drawings

(56) References Cited

FOREIGN PATENT DOCUMENTS

| | | |
|---|---|---|
| WO | 03024222 | 3/2003 |
| WO | 03027099 | 4/2003 |
| WO | 03062226 | 7/2003 |
| WO | 2004027042 | 4/2004 |
| WO | 2004033468 | 4/2004 |
| WO | 2004046129 | 6/2004 |
| WO | 2004067528 | 8/2004 |
| WO | 2005077934 | 8/2005 |
| WO | 2005085234 | 9/2005 |
| WO | 2005/113506 | 12/2005 |
| WO | 2005118552 | 12/2005 |
| WO | 2006/004903 | 1/2006 |
| WO | 2006000336 | 1/2006 |
| WO | 2006023783 | 3/2006 |
| WO | 2006040113 | 4/2006 |
| WO | 2006111341 | 10/2006 |
| WO | 2007006670 | 1/2007 |
| WO | 2007020877 | 2/2007 |
| WO | 2007024833 | 3/2007 |
| WO | 2007043677 | 4/2007 |
| WO | 2007/068356 | 6/2007 |
| WO | 2007144100 | 12/2007 |
| WO | WO 2007144100 A1 * | 12/2007 |
| WO | 2008/126858 | 10/2008 |
| WO | 2008126889 | 10/2008 |
| WO | 2008126890 | 10/2008 |
| WO | 2008126933 | 10/2008 |

OTHER PUBLICATIONS

Rostom et al.; "Azole Antimicrobial Pharmacophore-Based Tetrazoles: Synthesis and Biological Evaluation as Potential Antimicrobial and Anticonvulsant Agents"; Bioorganic & Medicinal Chemistry 17; 2009; pp. 2410-2422.

Gagnon et al; "Investigation on the Role of the Tetrazole in the Binding of Thiotetrazolylacetanilides With HIV-1 Wild Type and K103N/Y181C Double Mutant Reverse Transcriptases"; Bioorganic & Medicinal Chemistry Letters 19; 2009; pp. 1199-1205.

Baumgarth et al.; "Bicyclic Acylguanidine NA+/H+ Antiporter Inhibitors"; J. Med. Chem.; 1998; 41; pp. 3736-3747.

Hirashima et al.; "Benzimidazole Derivatives Bearing Substituted Biphenyls Substituted Biphenyls as Hepatitis C Virus NS5B RNA-Dependent RNA Polymerase Inhibitors: Structure-Activity Relationship Studies and Identification of a Potent and Highly Selective Inhibitor JTK-109"; J. Med. Chem.; 2006; 49; pp. 4721-4736.

Baur et al.; "Polydisperse Ethoxylated Fatty Alcohol Surfactants as Accelerators of Cuticular Penetration. 1. Effects of Ethoxy Chain Length and the Size of the Penetrants"; Pestic. Sci.; 1997; 51; pp. 131-152.

International Search Report Based on PCT/EP2011/059696 Mailed July 22, 2011.

* cited by examiner

ANTHRANILIC ACID DERIVATIVES

CROSS REFERENCE TO RELATED APPLICATIONS

This application claims priority to EP 10166062.9 filed Jun. 15, 2010 and U.S. Provisional Application No. 61/354,895 filed Jun. 15, 2010, the contents of which are incorporated herein by reference in their entireties.

BACKGROUND

1. Field of the Invention

The present invention relates to novel anthranilic acid derivatives, to their use as insecticides and acaricides for controlling animal pests, also in combination with other agents for activity boosting, and to a plurality of processes for their preparation.

2. Description of Related Art

Anthranilic acid derivatives having insecticidal properties have already been described in the literature, as for example in WO 01/70671, WO 03/015519, WO 03/016284, WO 03/015518, WO 03/024222, WO 03/016282, WO 03/016283, WO 03/062226, WO 03/027099, WO 04/027042, WO 04/033468, WO 2004/046129, WO 2004/067528, WO 2005/118552, WO 2005/077934, WO 2005/085234, WO 2006/023783, WO 2006/000336, WO 2006/040113, WO 2006/111341, WO 2007/006670, WO 2007/024833, WO2007/020877, WO 2007/144100, WO2007/043677, WO2008/126889, WO2008/126890 and WO2008/126933.

In their application, however, the active compounds already known in accordance with the specifications identified above have disadvantages in some respects, whether it be that they exhibit a narrow spectrum of application or whether it be that they do not have satisfactory insecticidal or acaricidal activity.

SUMMARY

Novel anthranilic acid derivatives have now been found which have advantages over the compounds already known, examples being better biological or environmental properties, broader application methods, an improved insecticidal or acaricidal activity, and also high compatibility with useful plants. The anthranilic acid derivatives can be used in combination with other agents for improving the efficacy in particular against insects which are difficult to control.

The present invention accordingly provides novel anthranilic acid derivatives of the formula (I)

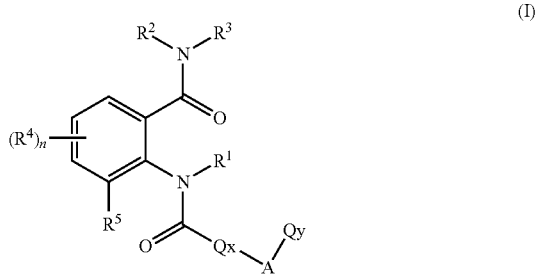

(I)

in which $R^1$ represents hydrogen, amino, hydroxyl or represents $C_1$-$C_6$-alkyl, $C_2$-$C_6$-alkenyl, $C_2$-$C_6$-alkynyl or $C_3$-$C_6$-cycloalkyl, each of which is optionally mono- or polysubstituted by identical or different substituents, where the substituents independently of one another may be selected from the group consisting of halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di-($C_1$-$C_4$-alkyl)amino, $C_3$-$C_6$-cycloalkylamino and ($C_1$-$C_4$-alkyl)-$C_3$-$C_6$-cycloalkylamino, $R^2$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkylamino, di-($C_1$-$C_4$-alkyl)amino, $C_3$-$C_6$-cycloalkylamino, $C_1$-$C_6$-alkoxycarbonyl or $C_1$-$C_6$-alkylcarbonyl, $R^3$ represents hydrogen or represents optionally mono- or polysubstituted $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, where the substituents are identical or different and independently of one another may be selected from the group consisting of halogen, cyano, (C=O)OH, (C=O)NH$_2$, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_2$-$C_6$-alkoxycarbonyl, $C_2$-$C_6$-alkylcarbonyl, $C_3$-$C_6$-trialkylsilyl or represents a phenyl ring or a 5- or 6-membered unsaturated, partially saturated or saturated heterocycle, where the phenyl ring or heterocycle is optionally mono- or polysubstituted by identical or different substituents and where the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, (C=O)NH$_2$, NO$_2$, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)alkylsilyl, ($C_1$-$C_4$-alkyl)($C_1$-$C_4$-alkoxy)imino, or $R^3$ represents $C_1$-$C_6$-alkoxycarbonyl, $C_1$-$C_6$-alkylcarbonyl, $C_1$-$C_6$-alkylaminocarbonyl or di($C_1$-$C_6$)alkylaminocarbonyl, or $R^3$ represents a phenyl ring or a 5- or 6-membered unsaturated, partially saturated or saturated heterocycle, where the phenyl ring or heterocycle is optionally mono- or polysubstituted by identical or different substituents and where the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, (C=O)NH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)alkylsilyl, ($C_1$-$C_4$-alkyl)($C_1$-$C_4$-alkoxy)imino, or $R^2$ and $R^3$ may be joined to one another via two to six carbon atoms and form a ring which optionally additionally contains a further nitrogen, sulphur or oxygen atom and may optionally be mono- to tetrasubstituted by $C_1$-$C_2$-alkyl, $C_1$-$C_2$-haloalkyl, halogen, cyano, amino $C_1$-$C_2$-alkoxy or $C_1$-$C_2$-haloalkoxy, $R^2$, $R^3$ furthermore together represent =S($C_1$-$C_4$-alkyl)$_2$, =S(O)($C_1$-$C_4$-alkyl)$_2$, $R^4$ represents hydrogen, halogen, cyano, nitro, hydroxyl, amino, carboxyl, OCN, SCN, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-alkoxy-$C_1$-$C_4$-alkyl, $C_1$-$C_4$-haloalkoxy, $SF_5$, $C_1$-$C_4$-alkylthio, $C_1$-$C_4$-alkylthio-$C_1$-$C_4$-alkyl, $C_1$-$C_4$-alkylsulphinyl, $C_1$-$C_4$-alkylsulphonyl, $C_1$-$C_4$-alkylsulphonyloxy, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_1$-$C_4$-alkylcarbonylamino, N-methoxy-N-methylamino, $C_1$-$C_4$-alkoxycarbonyl, $C_1$-$C_4$-alkoxycarbonyl-$C_1$-$C_4$-alkyl, $C_1$-$C_4$-alkylcarbonyl, $C_1$-$C_4$-alkylcarbonyloxy, aminocarbonyl, $C_1$-$C_4$-alkylaminocarbonyl, $C_1$-$C_4$-dialkylaminocarbonyl, aminothiocarbonyl, $C_1$-$C_4$-alkylaminothiocarbonyl, $C_1$-$C_4$-dialkylaminothiocarbonyl, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino, $C_1$-$C_4$-alkylsulphonylamino, aminosulphonyl, $C_1$-$C_4$-alkylaminosulphonyl, $C_1$-$C_4$-dialkylaminosulphonyl, $C_1$-$C_4$-alkylsulphoximino, $C_3$-$C_6$-trialkylsilyl or represents a 3- to 6-membered saturated, partially saturated or aromatic ring which may optionally contain one to three heteroatoms from the group consisting of O, S and N and which may optionally be mono- or polysubstituted by identical or different substituents from the group consisting of halogen, cyano, nitro, hydroxyl, amino, carboxyl, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphonyloxy, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_1$-$C_4$-alkylcarbonylamino, $C_1$-$C_4$-alkoxycarbonyl, $C_1$-$C_4$-alkylcarbonyl, $C_1$-$C_4$-alkylcarbonyloxy, aminocarbonyl, $C_1$-$C_4$-alkylaminocarbonyl, $C_1$-$C_4$-dialkylaminocarbonyl, aminothiocarbonyl, $C_1$-$C_4$-alkylaminothiocarbonyl, $C_1$-$C_4$-dialkylaminothiocarbonyl, $C_3$-$C_6$-cycloalkylamino, $C_1$-$C_4$-alkylsulphonylamino, aminosulphonyl, $C_1$-$C_4$-alkylaminosulphonyl and $C_1$-$C_4$-dialkylaminosulphonyl, two radicals $R^4$ form, via adjacent carbon atoms, a ring which represents —$(CH_2)_3$—, —$(CH_2)_4$—, —$(CH_2)_5$—, —(CH=CH—)$_2$—, —$OCH_2O$—, —O—$(CH_2)_2$—, —$OCF_2O$—, —$(CF_2)_2$—, —$O(CF_2)_2$—, —(CH=CH—CH=N)— or —(CH=CH—N=CH)—, or two radicals $R^4$ furthermore form, via adjacent carbon atoms, the fused rings below which are optionally mono- or polysubstituted by identical or different substituents, where the substituents independently of one another may be selected from the group consisting of hydrogen, cyano, $C_1$-$C_6$-alkyl, $C_3$-$C_6$-cycloalkyl, $C_1$-$C_6$-haloalkyl, $C_3$-$C_6$-halocycloalkyl, halogen, $C_1$-$C_6$-alkoxy, $C_1$-$C_4$-alkylthio($C_1$-$C_6$-alkyl), $C_1$-$C_4$-alkylsulphinyl($C_1$-$C_6$-alkyl), $C_1$-$C_4$-alkylsulphonyl($C_1$-$C_6$-alkyl), $C_1$-$C_4$-alkylamino, di-($C_1$-$C_4$-alkyl)amino and $C_3$-$C_6$-cycloalkylamino,

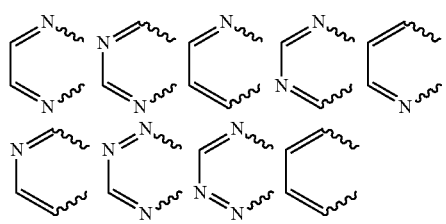

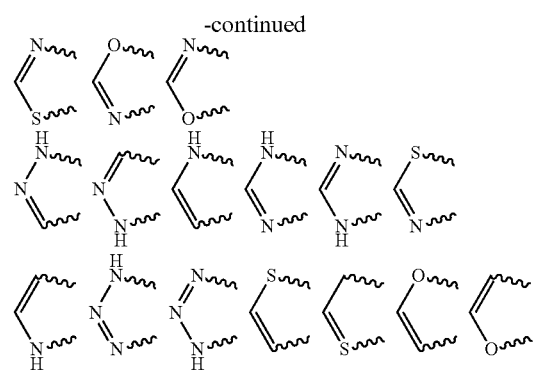

n represents 0 to 3, $R^5$ represents $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $Q_X$ represents an aromatic or heteroaromatic 5- or 6-membered ring which may contain 1-3 heteroatoms from the group consisting of N, S, O and which is optionally mono- or polysubstituted by identical or different $R^7$ substituents, where the radical R7 is attached via carbon if the ring is five-membered and contains exactly two nitrogen atoms which are adjacent, A represents optionally mono- or polysubstituted —($C_1$-$C_6$-alkylene)-, —($C_2$-$C_6$-alkenylene)-, —($C_2$-$C_6$-alkynylene)-, —$R^8$—($C_3$-$C_6$-cycloalkyl)-$R^8$—, —$R^8$—O—$R^8$—, —$R^8$—S—$R^8$—, —$R^8$—S(=O)—$R^8$—, —$R^8$—S(=O)$_2$—$R^8$—, —$R^8$—N($C_1$-$C_6$-alkyl)-$R^8$—, $R^8$—C=NO($C_1$-$C_6$-alkyl)-$R^8$, —CH[$CO_2$($C_1$-$C_6$-alkyl)-, —$R^8$—C(=O)—$R^8$, —$R^8$—C(=O)NH—$R^8$, $R^8$—C(=O)N($C_1$-$C_6$-alkyl)-$R^8$, —$R^8$—C(=O)NHNH—$R^8$—, —$R^8$—C(=O)N($C_1$-$C_6$-alkyl)-NH—$R^8$—, —$R^8$—C(=O)NHN($C_1$-$C_6$-alkyl)-$R^8$, —$R^8$—O(C=O)—$R^8$, —$R^8$—O(C=O)NH—$R^8$, —$R^8$—O(C=O)N($C_1$-$C_6$-alkyl)-$R^8$, —$R^8$—S(=O)$_2$NH—$R^8$, —$R^8$—(=O)$_2$N($C_1$-$C_6$-alkyl)-$R^8$, —$R^8$—S(C=O)—$R^8$, —$R^8$—S(C=O)NH—$R^8$, —$R^8$—S(C=O)N($C_1$-$C_6$-alkyl)-$R^8$, —$R^8$—NHNH—$R^8$, —$R^8$—NHN($C_1$-$C_6$-alkyl)-$R^8$, —$R^8$—N($C_1$-$C_6$-alkyl)-NH—$R^8$, —$R^8$—N($C_1$-$C_6$-alkyl)-N($C_1$-$C_6$-alkyl)-$R^8$, —$R^8$—N=CH—O—$R^8$, —$R^8$—NH(C=O)O—$R^8$, —$R^8$—N($C_1$-$C_6$-alkyl)-(C=O)O—$R^8$, —$R^8$—NH(C=O)NH—$R^8$, —$R^8$—NH(C=S)NH—$R^8$, —$R^8$—NHS(=O)$_2$—$R^8$, $R^8$—NH—$R^8$, $R^8$—C(=O)—C(=O)—$R^8$, $R^8$—C(OH)—$R^8$, $R^8$—NH(C=O)—$R^8$, $R^8$-Qz-$R^8$, $R^8$—C(=N—NR'$_2$)—$R^8$, $R^8$—C(=C—R'$_2$)—$R^8$ or —$R^8$—N($C_1$-$C_6$-alkyl)S(=O)$_2$—$R^8$, where the substituents independently of one another may be selected from the group consisting of halogen, cyano, nitro, hydroxyl, C1-C6-alkyl, C1-C6-alkyoxy, halo-C1-C6-alkyl, amino, (C1-C6-alkyl)amino, di($C_1$-$C_6$-alkyl)amino, C3-C6-cyclo where —($C_3$-$C_6$-cycloalkyl)- in the ring may optionally contain 1 or 2 heteroatoms selected from the group consisting of N, S, O, $R^8$ represents straight-chain or branched —($C_1$-$C_6$-alkylene)- or represents a direct bond, where a plurality of $R^8$ radicals independently of one another represent straight-chain or branched —($C_1$-$C_6$-alkylene)- or represent a direct bond, for example, $R^8$—O—$R^8$— represents —($C_1$-$C_6$-alkylene)-O—($C_1$-$C_6$-alkylene)-, —($C_1$-$C_6$-alkylene)-O—, —O—($C_1$-$C_6$-alkylene)-, or —O—, where R' represents alkyl, alkylcarbonyl, alkenyl, alkynyl which may optionally be mono- or polysubstituted by halogen, Qz represents a 3- or 4-membered partially saturated or saturated ring or a 5- or 6-membered partially saturated, saturated or aromatic ring or represents a 6- to 10-membered bicyclic ring system, where the ring or the bicyclic ring system may optionally contain 1-3 heteroatoms from the group consisting of N, S, O, where the ring or the bicyclic ring system is optionally mono- or polysubstituted by identical or different substituents, and where the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, $Q_Y$ represents a 5- or 6-membered partially saturated or saturated heterocyclic or heteroaromatic ring or an aromatic 8-, 9- or 10-membered fused heterobicyclic ring system, where the ring or the ring system is optionally mono- or polysubstituted by identical or different substituents, and where the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-halo, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)amino carbonyl, di-($C_1$-$C_4$-alkyl)aminocarbonyl, tri-($C_1$-$C_2$) alkylsilyl, ($C_1$-$C_4$-alkyl)($C_1$-$C_4$-alkoxy)imino, or where the substituents independently of one another may be selected from the group consisting of phenyl and a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy, $C_1$-$C_4$-haloalkoxy, $R^7$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_3$-$C_6$-cycloalkoxy or

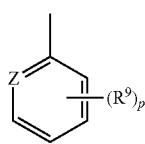

$R^9$ independently represents hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, p represents 0 to 4, Z represents N, CH, CF, CCl, CBr or CI, the compounds of the general formula (I) furthermore comprise N-oxides and salts.

If appropriate, the compounds of the formula (I) may be present in various polymorphic forms or as mixtures of different polymorphic forms. Both the pure polymorphs and the polymorph mixtures are provided by the invention and can be used according to the invention.

The compounds of the formula (I) optionally include diastereomers or enantiomers.

DETAILED DESCRIPTION OF A PREFERRED EMBODIMENT

The formula (I) provides a general definition of the compounds according to the invention. Preferred, particularly preferred and very particularly preferred are compounds of the formula (I) in which R1 preferably represents hydrogen, C1-C6-alkyl, C2-C6-alkenyl, C2-C6-alkynyl, C3-C6-cycloalkyl, cyano(C1-C6-alkyl), C1-C6-haloalkyl, $C_2$-$C_6$-haloalkenyl, $C_2$-$C_6$-haloalkynyl, C1-C4-alkoxy-C1-C4-alkyl, $C_1$-$C_4$-alkylthio-$C_1$-$C_4$-alkyl, C1-C4-alkylsulphinyl-$C_1$-$C_4$-alkyl or $C_1$-$C_4$-alkylsulphonyl-$C_1$-$C_4$-alkyl, $R^1$ particularly preferably represents hydrogen, methyl, ethyl, cyclopropyl, cyanomethyl, methoxymethyl, methylthiomethyl, methylsulphinylmethyl or methylsulphonylmethyl, $R^1$ very particularly preferably represents hydrogen, $R^2$ preferably represents hydrogen or $C_1$-$C_6$-alkyl.

$R^2$ particularly preferably represents hydrogen or methyl.

$R^2$ very particularly preferably represents hydrogen, $R^3$ preferably represents hydrogen or represents in each case optionally mono- or polysubstituted $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, where the substituents are identical or different and independently of one another may be selected from the group consisting of halogen, cyano, (C=O)OH, (C=O)$NH_2$, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_2$-$C_6$-alkoxycarbonyl, $C_2$-$C_6$-alkylcarbonyl or represents a phenyl ring or a 5- or 6-membered unsaturated, partially saturated or saturated heterocycle, where the phenyl ring or heterocycle is optionally mono- or polysubstituted by identical or different substituents and where the substituents independently of one another may be selected from the group consisting of hydrogen, $C_1$-$C_6$alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, (C=O)$NH_2$, $NO_2$, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, or $R^3$ preferably represents $C_2$-$C_4$-alkoxycarbonyl, $C_2$-$C_4$-alkylcarbonyl, $C_2$-$C_4$-alkylaminocarbonyl or $C_2$-$C_4$-dialkylaminocarbonyl, or $R^3$ preferably represents a phenyl ring or a 5- or 6-membered unsaturated, partially saturated or saturated heterocycle, where the phenyl ring or heterocycle is optionally mono- or polysubstituted by identical or different substituents and where the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, (C=O)NH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, $R^3$ particularly preferably represents hydrogen or represents in each case optionally mono- or polysubstituted $C_1$-$C_6$-alkyl, $C_1$-$C_6$-alkoxy or $C_3$-$C_6$-cycloalkyl, where the substituents are identical or different and independently of one another may be selected from the group consisting of halogen, cyano, (C=O)OH, (C=O)NH$_2$, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_2$-$C_6$-alkoxycarbonyl, $C_2$-$C_6$-alkylcarbonyl or represents a phenyl ring or a 5- or 6-membered unsaturated, partially saturated or saturated heterocycle, where the phenyl ring or heterocycle is optionally mono- or polysubstituted by identical or different substituents and where the substituents independently of one another may be selected from the group consisting of hydrogen, $C_1$-$C_6$-alkyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl or $R^3$ particularly preferably represents $C_2$-$C_4$-alkoxycarbonyl, $C_2$-$C_4$-alkylcarbonyl, $C_2$-$C_4$-alkylaminocarbonyl, or $R^3$ particularly preferably represents a phenyl ring or a 5- or 6-membered unsaturated, partially saturated or saturated heterocycle, where the phenyl ring or heterocycle is optionally mono- or polysubstituted by identical or different substituents and where the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)NH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, or $R^3$ very particularly preferably represents hydrogen, $C_1$-$C_4$-alkyl (methyl, ethyl, n-propyl, isopropyl, n-butyl, isobutyl, sec-butyl or tert-butyl), cyclopropyl, cyclobutyl, cyano-$C_1$-$C_3$-alkyl (cyanomethyl, 1-cyanoethyl, 2-cyanoethyl, 1-cyano-n-propyl, 2-cyano-n-propyl, 3-cyano-n-propyl, 1-cyanoisopropyl, 2-cyanoisopropyl), phenyl, pyridyl, or $R^3$ especially preferably represents hydrogen, methyl, isopropyl, cyclopropyl, tert-butyl or cyanomethyl.

$R^4$ preferably represents hydrogen, $C_1$-$C_4$-alkyl, $C_1$-$C_4$-haloalkyl, halogen, cyano, $C_1$-$C_4$-alkoxy, $C_1$-$C_4$-haloalkoxy, $C_1$-$C_4$-alkylthio or $C_1$-$C_4$-haloalkylthio, two adjacent radicals $R^4$ likewise preferably represent —(CH$_2$)$_3$—, —(CH$_2$)$_4$—, —(CH$_2$)$_5$—, —(CH=CH—)$_2$—, —OCH$_2$O—, —O(CH$_2$)$_2$O—, —OCF$_2$O—, —(CF$_2$)$_2$O—, —O(CF$_2$)$_2$O—, —(CH=CH—CH=N)— or —(CH=CH—N=CH)—, $R^4$ particularly preferably represents hydrogen, $C_1$-$C_4$-alkyl, $C_1$-$C_2$-haloalkyl, halogen, cyano or $C_1$-$C_2$-haloalkoxy, two adjacent radicals $R^4$ particularly preferably represent —(CH$_2$)$_4$—, —(CH=CH—)$_2$—, —O(CH$_2$)$_2$O—, —O(CF$_2$)$_2$O—, —(CH=CH—CH=N)— or —(CH=CH—N=CH)—, $R^4$ very particularly preferably represents hydrogen, methyl, trifluoromethyl, cyano, fluorine, chlorine, bromine, iodine or trifluoromethoxy. Moreover, two adjacent radicals $R^4$ very particularly preferably represent —(CH$_2$)$_4$— or —(CH=CH—)$_2$—.

$R^4$ especially preferably represents chlorine, fluorine or bromine, $R^4$ furthermore especially preferably represents iodine or cyano.

two adjacent radicals $R^4$ especially preferably represent —(CH=CH—)$_2$ $R^5$ preferably represents $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $R^5$ particularly preferably represents $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluorine, chlorine, bromine, iodine, cyano, nitro or $C_3$-$C_6$-trialkylsilyl, $R^5$ very particularly preferably represents methyl, fluorine, chlorine, bromine or iodine, $R^5$ especially preferably represents methyl or chlorine, $Q_X$ preferably represents a heteroaromatic 5-membered ring which may contain 1-3 heteroatoms from the group consisting of N, S, O and which is optionally mono- or polysubstituted by identical or different $R^7$ substituents, where the radical $R^7$ is attached via carbon if the ring is five-membered and contains exactly two nitrogen atoms which are adjacent, or represents a heteroaromatic 6-membered ring which may contain 1-3 nitrogen atoms, or represents phenyl, $Q_X$ particularly preferably represents a 5- or 6-membered ring which is optionally mono- or polysubstituted by identical or different $R^7$ substituents and is selected from the group consisting of furan, thiophene, triazole, imidazole, thiazole, oxazole, isoxazole, isothiazole, thiadiazole, oxadiazole, pyrrole, pyridine, pyrimidine, pyridazine, pyrazine, phenyl or represents pyrazole where the radical $R^7$ is attached via carbon to the pyrazole, $Q_X$ very particularly preferably represents thiazole, oxazole, pyrrole, imidazole, triazole, pyrimidine, phenyl or represents pyrazole where the radical $R^7$ is attached via carbon to the pyrazole, which is monosubstituted by the group $R^7$

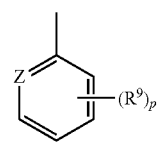

where Z, R and p may have the general meanings given above or the preferred or particularly preferred meanings given below, A preferably represents optionally mono- or polysubstituted —($C_1$-$C_4$alkylene)-, —($C_2$-$C_4$-alkenylene)-, —($C_2$-$C_4$-alkynylene)-, —$R^8$—($C_3$-$C_6$-cycloalkyl)-$R^8$—, —$R^8$—O—

R$^8$—, —R$^8$—S—R$^8$—, —R$^8$—S(=O)—R$^8$—, —R$^8$—S(=O)$_2$—R$^8$—, —R$^8$—C=NO(C$_1$-C$_4$-alkyl), —R$^8$—C(=O)—R$^8$, —R$^8$—C(=S)—R$^8$, —R$^8$—C(=O)NH—R$^8$, R$^8$—C(=O)N(C$_1$-C$_4$-alkyl)-R$^8$, —R$^8$—S(=O)$_2$NH—R$^8$, —R$^8$—S(=O)$_2$N(C$_1$-C$_4$-alkyl)-R$^8$, —R$^8$—NH(C=O)O—R$^8$, —R$^8$—N(C$_1$-C$_4$-alkyl)-(C=O)O—R$^8$, —R$^8$—NH(C=O)NH—R$^8$, —R$^8$—NHS(=O)$_2$—R$^8$, —R$^8$—N(C$_1$-C$_4$-alkyl)S(=O)$_2$—R$^8$, R$^8$—NH—R$^8$, R$^8$C(=O)—C(=O)—R$^8$, R$^8$C(OH)—R$^8$, R$^8$-Qz-R$^8$, where the substituents independently of one another may be selected from the group consisting of halogen, cyano, nitro, hydroxyl, C$_1$-C$_6$-alkyl, C$_1$-C$_6$-alkyoxy and halo-C$_1$-C$_6$-alkyl, where Qz may have the general meanings given above or the preferred or particularly preferred meanings given below, A particularly preferably represents —CH$_2$—, —CH$_2$O—, —CH$_2$OCH$_2$—, —CH$_2$S—, —CH$_2$SCH$_2$—, —CH$_2$N(C$_1$-C$_4$-alkyl)-, —CH$_2$N(C$_1$-C$_4$-alkyl)CH$_2$—, —CH(Hal)-, —C(Hal)$_2$-, —CH(CN)—, CH$_2$(CO)—, CH$_2$(CS)—, CH$_2$CH(OH)—, -cyclopropyl-, CH$_2$(CO)CH$_2$—, —CH(C$_1$-C$_4$-alkyl)-, —C(di-C$_1$-C$_6$-alkyl)-, —CH$_2$CH$_2$—, —CH=CH—, —C≡C—, —C=NO(C$_1$-C$_6$-alkyl), —C(=O)(C$_1$-C$_4$-alkyl)-, A very particularly preferably represents —CH$_2$—, —CH(CH$_3$), C(CH$_3$)$_2$, —CH$_2$CH$_2$—, —CH(CN)—, —CH$_2$O— or —C(=O)—CH$_2$—, A especially preferably represents CH$_2$, CH(CH$_3$), —CH$_2$O— or —C(=O)—CH$_2$—, Qz preferably represents a 3- or 4-membered partially saturated or saturated ring or represents a 5- or 6-membered partially saturated, saturated or aromatic ring, where the ring may optionally contain 1-3 heteroatoms from the group consisting of N, S, O, where the ring is optionally mono- or polysubstituted by identical or different substituents and where the substituents independently of one another may be selected from the group consisting of hydrogen, C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, CN, OH, C$_1$-C$_4$-alkoxy, C$_1$-C$_4$-haloalkoxy, C$_1$-C$_4$-alkylthio, C$_1$-C$_4$-alkylsulphinyl, C$_1$-C$_4$-alkylsulphonyl, C$_1$-C$_4$-haloalkylthio, C$_1$-C$_4$-halo, C$_1$-C$_4$-haloalkylsulphonyl, Qz particularly preferably represents a 3- to 4-membered, partially saturated or saturated ring or represents a 5-membered partially saturated, saturated or aromatic ring, where the ring may optionally contain 1-2 heteroatoms from the group consisting of N, S, O, where the ring is optionally mono- or polysubstituted by identical or different substituents and where the substituents independently of one another may be selected from the group consisting of hydrogen, C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, CN, OH, C$_1$-C$_4$-alkoxy, C$_1$-C$_4$-haloalkoxy, C$_1$-C$_4$-alkylthio, C$_1$-C$_4$-alkylsulphinyl, C$_1$-C$_4$-alkylsulphonyl, C$_1$-C$_4$-haloalkylthio, C$_1$-C$_4$-haloalkylsulphinyl, C$_1$-C$_4$-haloalkylsulphonyl, Qz very particularly preferably represents azetidine, oxetane or thietane, pyrrolidine, pyrroline, pyrazolidine, pyrazoline, imidazolidine, imidazolidone, imidazoline, tetrahydrofuran, tetrahydrothiophene, thiazolidine, isothiazolidine, isoxazoline, which are optionally mono- or polysubstituted by identical or different substituents, where the substituents independently of one another may be selected from the group consisting of hydrogen, methyl, ethyl, isopropyl, hydroxyl, methoxy, trifluoromethoxy, fluorine, chlorine, bromine, cyano, difluoromethyl, trifluoromethyl, R$^7$ preferably represents C$_1$-C$_6$-alkyl or represents the radical

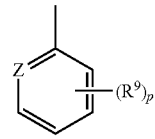

R$^7$ furthermore preferably represents C$_3$-C$_6$-cycloalkoxy,

R$^7$ particularly preferably represents methyl or represents the radical

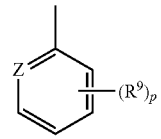

R$^9$ independently preferably represents hydrogen, halogen, cyano, C$_1$-C$_4$-alkyl, C$_1$-C$_4$-alkoxy, C$_1$-C$_4$-haloalkyl, C$_1$-C$_4$-haloalkoxy, C$_1$-C$_4$-haloalkylsulphonyl or (C$_1$-C$_4$-alkyl)-C$_1$-C$_4$-alkoxyimino, R$^9$ independently particularly preferably represents hydrogen, halogen, CN or C$_1$-C$_4$-haloalkyl, R$^9$ independently very particularly preferably represents fluorine, chlorine or bromine, R$^9$ especially preferably represents chlorine, p preferably represents 1, 2 or 3, p particularly preferably represents 1 or 2, p very particularly preferably represents 1, Z preferably represents N, CH, CF, CCl, CBr or CI, Z particularly preferably represents N, CH, CF, CCl or CBr, Z very particularly preferably represents N, CCl or CH, R$^8$ preferably represents straight-chain or branched —(C$_1$-C$_4$-alkylene)- or represents a direct bond R$^8$ particularly preferably represents methyl, ethyl, propyl, isopropyl, n-butyl, sec-butyl or isobutyl or a direct bond R$^8$ very particularly preferably represents methyl or ethyl or a direct bond Q$_Y$ preferably represents a 5- or 6-membered partially saturated or saturated heterocyclic or heteroaromatic ring or an aromatic 8-, 9- or 10-membered fused heterobicyclic ring system where the heteroatoms may be selected from the group consisting of N, S, O, where the ring or the ring system is optionally mono- or polysubstituted by identical or different substituents and where the substituents independently of one another may be selected from the group consisting of hydrogen, C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, CN, CO$_2$H, CO$_2$NH$_2$, NO$_2$, OH, C$_1$-C$_4$-alkoxy, C$_1$-C$_4$-haloalkoxy, C$_1$-C$_4$-alkylthio, C$_1$-C$_4$-alkylsulphinyl, C$_1$-C$_4$-alkylsulphonyl, C$_1$-C$_4$-haloalkylthio, C$_1$-C$_4$-haloalkylsulphinyl, C$_1$-C$_4$-haloalkylsulphonyl, or where the substituents independently of one another may be selected from the group consisting of phenyl and a 5- or 6-membered heteroaromatic ring, where phenyl or the ring may optionally be mono- or polysubstituted by identical or different substituents from the group consisting of C$_1$-C$_6$-alkyl, C$_2$-C$_6$-alkenyl, C$_2$-C$_6$-alkynyl, C$_3$-C$_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy, $C_1$-$C_4$-haloalkoxy, $Q_Y$ particularly preferably represents an optionally mono- or polysubstituted 5- or 6-membered heteroaromatic ring from the group consisting of Q-1 to Q-53 and Q-58 to Q-59, Q62 to Q63, an aromatic 9-membered fused heterobicyclic ring system Q-54 to Q-56 or a 5-membered heterocyclic ring Q-60 to Q-61 where the substituents independently of one another may be selected from the group consisting of $C_1$-$C_3$-alkyl, $C_1$-$C_3$-haloalkyl, $C_1$-$C_2$-alkoxy, halogen, cyano, hydroxyl, nitro and $C_1$-$C_2$-haloalkoxy, or where the substituents independently of one another may be selected from the group consisting of phenyl and a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy, $C_1$-$C_4$-haloalkoxy, $Q_Y$ very particularly preferably represents an optionally mono- or polysubstituted 5- or 6-membered heteroaromatic ring from the group consisting of Q-36 to Q-40, Q43, Q-58 to Q-59, Q62, Q63, an aromatic 9-membered fused heterobicyclic ring system Q-54 to Q-56 or a 5-membered heterocyclic ring Q-60 to Q-61 where the substituents independently of one another may be selected from the group consisting of $C_1$-$C_3$-alkyl, $C_1$-$C_3$-haloalkyl, $C_1$-$C_2$-alkoxy, halogen, cyano, hydroxyl, nitro and $C_1$-$C_2$-haloalkoxy, or where the substituents independently of one another may be selected from the group consisting of phenyl and a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy, $C_1$-$C_4$-haloalkoxy, $Q_Y$ especially preferably represents an optionally mono- or polysubstituted heteroaromatic ring from the group consisting of Q-37, Q-38, Q-39, Q-40, Q43, Q-58, Q-59, Q62 and Q63 or a 5-membered heterocyclic ring Q-60 where the substituents are identical or different and independently of one another may be selected from the group consisting of methyl, ethyl, cyclopropyl, tert-butyl, chlorine, fluorine, iodine, bromine, cyano, nitro, difluoromethyl, trifluoromethyl, pentafluoroethyl, n-heptafluoropropyl and isoheptafluoropropyl or where the substituents independently of one another may be selected from the group consisting of phenyl and a 5- or 6-membered heteroaromatic ring, where the substituents independently of one another may be selected from the group consisting of methyl, ethyl, cyclopropyl, tert-butyl, chlorine, fluorine, iodine, bromine, cyano, nitro, difluoromethyl, trifluoromethyl, pentafluorethyl, n-heptafluoropropyl and iso-heptafluoropropyl,

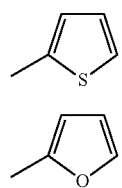
Q-1

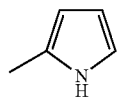
Q-2

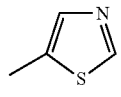
Q-3

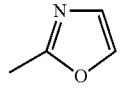
Q-4

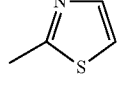
Q-5

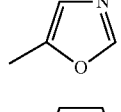
Q-6

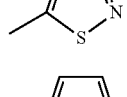
Q-7

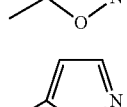
Q-8

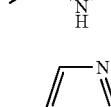
Q-9

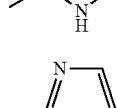
Q-10

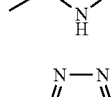
Q-11

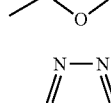
Q-12

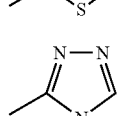
Q-13

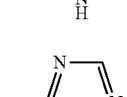
Q-14

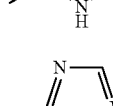
Q-15

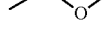
Q-16

Q-17

| | |
|---|---|
| Q-18 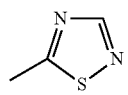 | Q-30 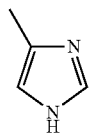 |
| Q-19 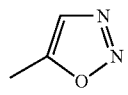 | Q-31  |
| Q-20  | Q-32 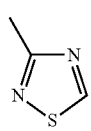 |
| Q-21  | Q-33 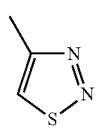 |
| Q-22 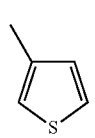 | Q-34 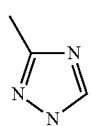 |
| Q-23 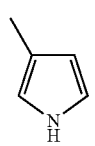 | Q-35 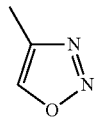 |
| Q-24 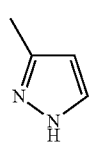 | Q-36 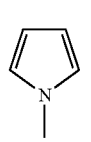 |
| Q-25 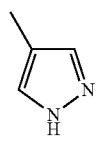 | Q-37 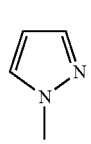 |
| Q-26 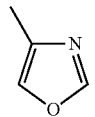 | Q-38 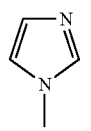 |
| Q-27 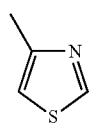 | Q-39 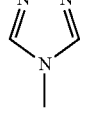 |
| Q-28 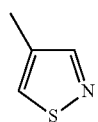 | Q-40 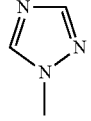 |
| Q-29 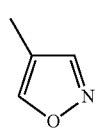 | Q-41 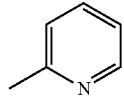 |

Q-42 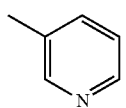

Q-43 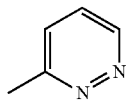

Q-44 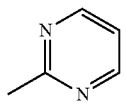

Q-45 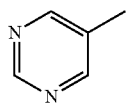

Q-46 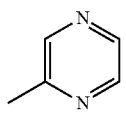

Q-47 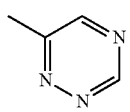

Q-48 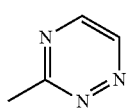

Q-49 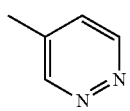

Q-50 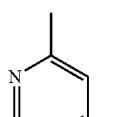

Q-51 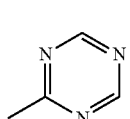

Q-52 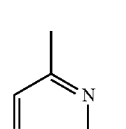

Q-53 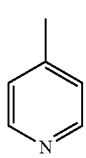

Q-54 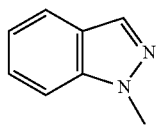

Q-55 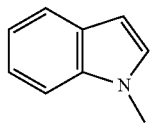

Q-56 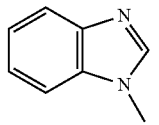

Q-57 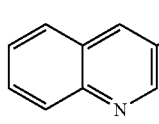

Q-58 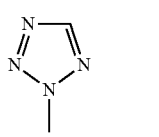

Q-59 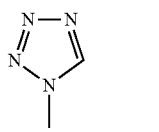

Q-60 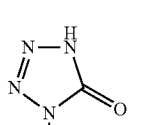

Q-61 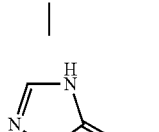

Q-62 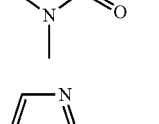

Q-63 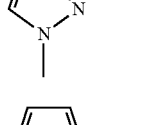

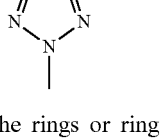

The rings or ring systems listed above may optionally independently of one another additionally be substituted by oxo, thioxo, (=O)=NH, (=O)=N—CN, (=O)$_2$. Examples which may be mentioned are tetrahydrothiophene dioxide, imidazolidone.

In this case, the oxo group as substituent at a ring carbon atom means, for example, a carbonyl group in the heterocyclic ring. This also preferably comprises lactones and lactams. The oxo group may also be present at the hetero ring atoms, which may exist in various oxidation levels, for example in the case of nitrogen and sulphur, in which case they form, for example, the divalent groups —N(O)—, —S(O)— (also abbreviated as SO) and —S(O)₂— (also abbreviated as SO₂) in the heterocyclic ring. In the case of —N(O)— and —S(O)— groups, in each case both enantiomers are included.

In a heterocyclic ring, substituents other than the oxo group can also be attached to a heteroatom, for example a nitrogen atom, if a hydrogen atom at the nitrogen atom of the skeleton is replaced in the process. In the case of the nitrogen atom and also other heteroatoms such as, for example, the sulphur atom, there may also be further substitution with formation of quaternary ammonium compounds or sulphonium compounds.

The above-recited general radical definitions and elucidations or those recited in preference ranges may be combined arbitrarily with one another, in other words including combinations between the respective ranges and preference ranges. They apply both to the end products and, correspondingly, to precursors and intermediates.

Preference in accordance with the invention is given to the compounds of the formula (I) which contain a combination of the meanings listed above as being preferred (preferably).

Particular preference according to the invention is given to the compounds of the formula (I) which contain a combination of the meanings listed above as being particularly preferred.

Very particular preference according to the invention is given to compounds of the formula (I) which contain a combination of the meanings listed above as being very particularly preferred.

The compounds of the formulae (I) may be present more particularly in the form of different regioisomers: for example in the form of mixtures of compounds where the attachment of the ring or the ring system Qy to the radical (A) is in each case via different carbon or nitrogen atoms.

Furthermore, for example, in the form of mixtures of compounds having the definition Q62 and Q63, respectively, or in the form of mixtures of compounds having the definition Q58 and Q59. The invention therefore also comprises mixtures of compounds of the formula (I) where QY has the meanings Q62 and Q63 and also Q58 and Q59 and the compounds may be present in various mixing ratios. Preference in this context is given to mixing ratios of the compounds of the formula (I) in which the radical QY is Q62 or Q58 to compounds of the formula (I) in which the radical QY is Q63 or Q59, of 60:40 to 99:1, particularly preferably of 70:30 to 98:2, very particularly preferably of 80:20 to 97:3. Especially preferred are the following mixing ratios for a compound of the formula (I) where QY has the definition Q62 or Q58 to the compound of the formula (I) where QY has the definition Q63 or Q59: 80:20; 81:19; 82:18; 83:17; 84:16; 85:15; 86:14; 87:13; 88:12; 89:11; 90:10, 91:9; 92:8; 93:7; 94:6; 95; 5; 96:4; 97:3.

Preparation Processes

The compounds of the general formula (I) can be obtained when (A) anilines of the formula (II)

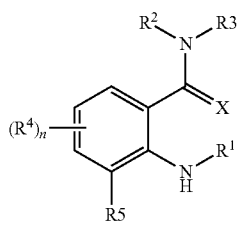

(II)

in which $R^1$, $R^2$, $R^3$, $R^4$, $R^5$ and n have the meanings given above and X represents O, are reacted, for example, with carbonyl chlorides of the formula (III)

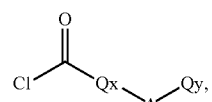

(III)

where
Qx, A and Qy have the meanings given above,
in the presence of an acid-binding agent; or
(B) anilines of the formula (II)

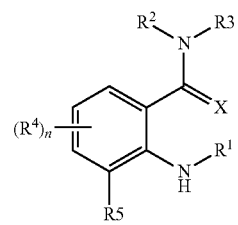

(II)

in which $R^1$, $R^2$, $R^3$, $R^4$, $R^5$ and n have the meanings given above and X represents O,
are reacted, for example, with a carboxylic acid of the formula (IV)

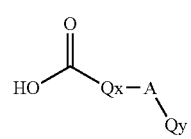

(IV)

where
Qx, A and Qy have the meanings given above,
in the presence of a condensing agent; or
(C) for the synthesis of anthranilamides of the formula (I) in which $R^1$ represents hydrogen,
for example, benzoxazinones of the formula (V)

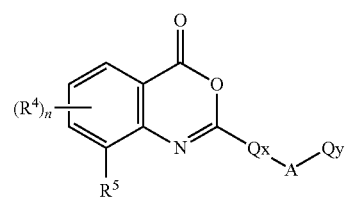

(V)

in which $R^4$, $R^5$, Qx, A, Qy and n have the meanings given above
are reacted with an amine of the formula (VI)

(VI)

in which $R^3$ has the meanings given above
in the presence of a diluent to give compounds of the formula (I) according to the invention.

In particular, compounds of the general formula (I),
in which Qx represents

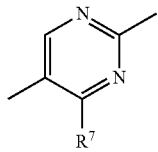

can be prepared when
(B-1) anilines of the formula (II)

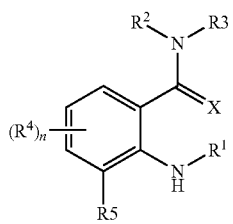

in which $R^1$, $R^2$, $R^3$, $R^4$, $R^5$ and n have the meanings given above are reacted, for example, with a carboxylic acid of the formula (IV-1)

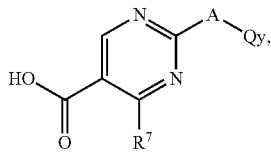

in which $R^7$, A and Qy have the meanings given above,
in the presence of a condensing agent.

Carboxylic acids of the formula (IV-1) can be prepared according to the reaction scheme below in which $R^7$, A, Qy have the meanings given above and R represents $C_1$-$C_6$-alkyl and Hal represents halogen from compounds of the formula (VIII). Compounds of the formula (VIII) are known (for example J. Med. Chem. 49, 2006, 4721-4736). The conversion of (VIII) into (IX) can be carried out by known methods (for example WO2005/113506). The further reaction via compounds of the formula X to compounds of the formula (IV-1) can be carried out by known methods (e.g. WO2007/144100).

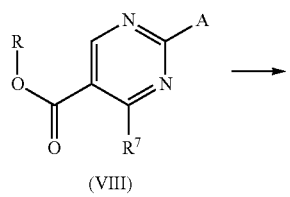

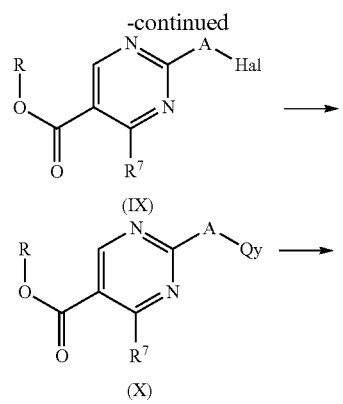

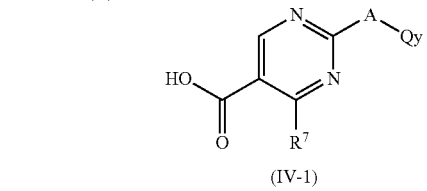

In particular, compounds of the general formula (I),
in which Qx represents

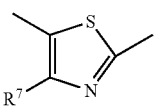

can be prepared when
(B-2) anilines of the formula (II)

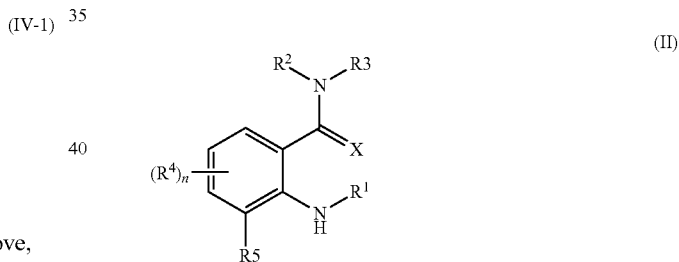

in which $R^1$, $R^2$, $R^3$, $R^4$, $R^5$, X and n have the meanings given above
are reacted, for example, with a carboxylic acid of the formula (IV-2)

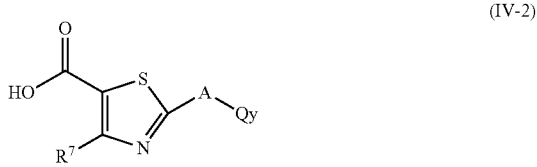

in which $R^7$, A and Qy have the meanings given above,
in the presence of a condensing agent.

Carboxylic acids of the formula (IV-2) can be prepared according to the reaction scheme below in which $R^7$, A and Qy have the meanings given above and R represents $C_1$-$C_6$-alkyl and Hal represents halogen from compounds of the formula (XI). Compounds of the formula (XI) are known (for example J. Med. Chem. 49, 2006, 4721-4736). The conversion of (XI) into (XII) can be carried out by known methods (e.g. WO2005/113506). The further reaction via XIII to carboxylic acids of the formula (IV-2) can be carried out by known methods (for example WO2007/144100).

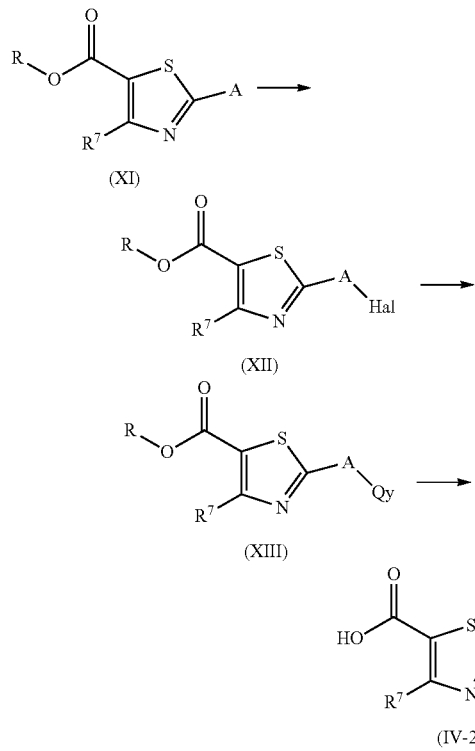

In particular, compounds of the general formula (I), in which Qx represents

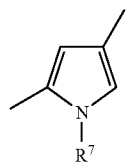

can be prepared by reacting
(B-3) anilines of the formula (II)

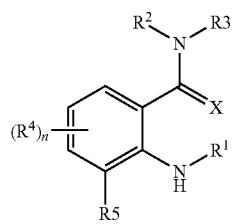

in which R1, R2, R3, R4, R5, X and n have the meanings given above
for example with a carboxylic acid of the formula (IV-3)

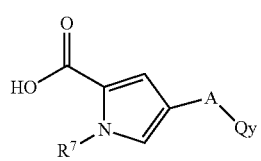

in which $R^7$, A and Qy have the meanings given above, in the presence of a condensing agent.

Carboxylic acids of the formula (IV-3) are novel. They can be prepared according to the reaction scheme below, where $R^7$ and $Q_y$ have the meanings given above and R represents $C_1$-$C_6$-alkyl, from compounds of the formula XIV. Compounds of the formula XIV are known (for example WO 2003016283). The conversion of compounds of the formula XIV into compounds of the formula XV can be carried out by known methods using, for example, (1-ethoxyvinyl)tributyl-stannane with palladium catalysis (for example J. Med. Chem. 41, 1998, 3736). The further conversion into compounds of the formula XVI is carried out using a suitable halogenating agent (for example Bioorganic & Medicinal Chemistry Letters, 19(4), 1199-1205; 2009). Coupling with Qy to give compounds of the formula XVII and hydrolysis to carboxylic acids of the formula IV-3 are carried out by known methods (for example Bioorganic & Medicinal Chemistry, 17(6), 2410-2422; 2009 and WO2006004903).

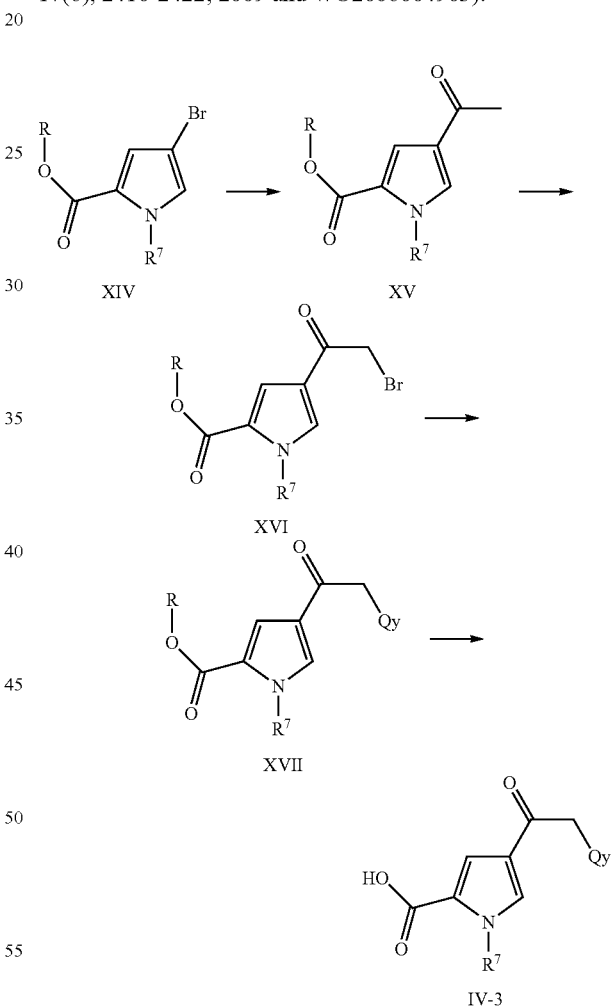

In particular, compounds of the general formula (I), in which Qx represents

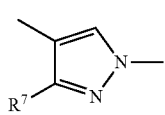

can be prepared when (B-4) anilines of the formula (II)

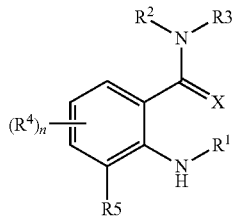

(II)

in which $R^1$, $R^2$, $R^3$, $R^4$, $R^5$, X and n have the meanings given above are reacted for example with a carboxylic acid of the formula (IV-4)

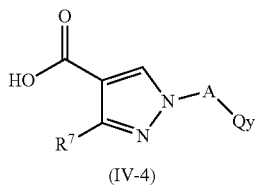

(IV-4)

in which $R^7$, A and Qy have the meanings given above, in the presence of a condensing agent.

Carboxylic acids of the formula (IV-4) can be prepared according to the reaction scheme below in which R7, A and Qy have the meanings given above and R represents $C_1$-$C_6$-alkyl and Hal represents halogen from compounds of the formula (XVIII) using (XIX). Compounds of the formula (XVIII) are known (for example WO 2007/043677) and commercially available. Compounds of the formula (XIX) are commercially available. The alkylation of (XVIII) with (XIX) can be carried out by known methods (for example Bioorg. Med. Chem. 2008, 16, 10165-10171). The further conversion of compounds of the formula (XX) into compounds of the formula (IV-4) can be carried out by known methods (for example WO2007/144100).

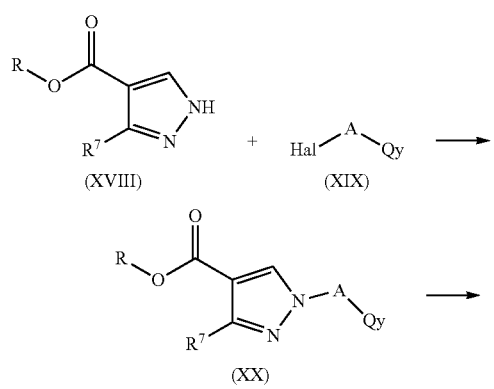

-continued

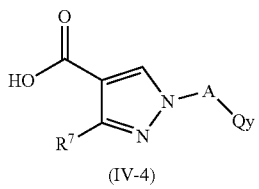

(IV-4)

In particular, compounds of the general formula (I), in which Qx represents

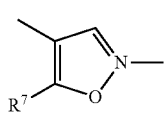

can be prepared when (B-5) anilines of the formula (II)

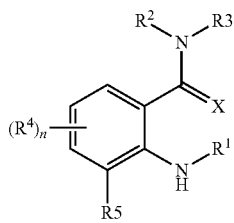

(II)

in which R1, R2, R3, R4, R5, X and n have the meanings given above are reacted for example with a carboxylic acid of the formula (IV-5)

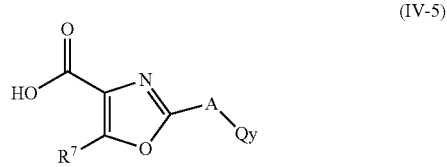

(IV-5)

in which R7, A and Qy have the meanings given above, in the presence of a condensing agent.

Carboxylic acids of the formula (IV-5) can be prepared according to the reaction scheme below in which R7, A and Qy have the meanings given above and R represents $C_1$-$C_6$-alkyl and Hal represents halogen from compounds of the formula (XXI). Compounds of the formula (XXI) are known and can be prepared by known methods (for example J. Med. Chem. 2006, 49, 4721-4736). The conversion of (XXI) into (XXII) can be carried out by known methods (for example WO2005/113506). The further conversion via (XXIII) into carboxylic acids of the formula (IV-5) can be carried out by known methods (for example WO2007/144100).

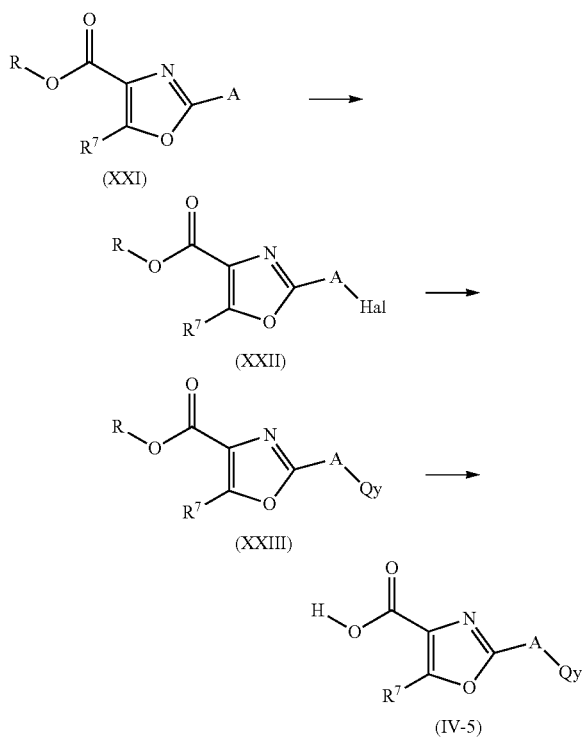

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro*, *Aceria sheldoni*, *Aculops* spp., *Aculus* spp., *Amblyomma* spp., *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Hemitarsonemus* spp., *Hyalomma* spp., *Ixodes* spp., *Latrodectus mactans*, *Metatetranychus* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apogonia* spp., *Atomaria* spp., *Attagenus* spp., *Bruchidius obtectus*, *Bruchus* spp., *Ceuthorhynchus* spp., *Cleonus mendicus*, *Conoderus* spp., *Cosmopolites* spp., *Costelytra zealandica*, *Curculio* spp., *Cryptorhynchus lapathi*, *Dermestes* spp., *Diabrotica* spp., *Epilachna* spp., *Faustinus cubae*, *Gibbium psylloides*, *Heteronychus arator*, *Hylamorpha elegans*, *Hylotrupes bajulus*, *Hypera postica*, *Hypothenemus* spp., *Lachnosterna consanguinea*, *Leptinotarsa decemlineata*, *Lissorhoptrus oryzophilus*, *Lixus* spp., *Lyctus* spp., *Meligethes aeneus*, *Melolontha melolontha*, *Migdolus* spp., *Monochamus* spp., *Naupactus xanthographus*, *Niptus hololeucus*, *Oryctes rhinoceros*, *Oryzaephilus surinamensis*, *Otiorrhynchus sulcatus*, *Oxycetonia jucunda*, *Phaedon cochleariae*, *Phyllophaga* spp., *Popillia japonica*, *Premnotrypes* spp., *Psylliodes chrysocephala*, *Ptinus* spp., *Rhizobius ventralis*, *Rhizopertha dominica*, *Sitophilus* spp., *Sphenophorus* spp., *Sternechus* spp., *Symphyletes* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp., *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., Loa Loa, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control protozoa, such as Eimeria.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus* arundinis, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis* and *Vespa* spp.

From the order of the Isopoda, for example, *Armadillidium vulgare*, *Oniscus asellus* and *Porcellio scaber*.

From the order of the Isoptera, for example, *Reticulitermes* spp. and *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia* kuehniella, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp. and *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni* and *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans* and *Xiphinema* spp.

The effectiveness of the compounds of the formula (I) can be increased by adding ammonium salts and phosphonium salts. The ammonium salts and phosphonium salts are defined by formula (XI)

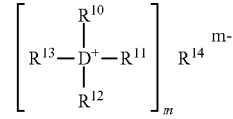

(XXIV)

in which

D represents nitrogen or phosphorus,

D preferably represents nitrogen, $R^{10}$, $R^{11}$, $R^{12}$ and $R^{13}$ independently of one another represent hydrogen or in each case optionally substituted $C_1$-$C_8$-alkyl or mono- or polyunsaturated, optionally substituted $C_1$-$C_8$-alkylene where the substituents may be selected from the group consisting of halogen, nitro and cyano, $R^{10}$, $R^{11}$, $R^{12}$ and $R^{13}$ preferably independently of one another represent hydrogen or in each case optionally substituted $C_1$-$C_4$-alkyl, where the substituents may be selected from the group consisting of halogen, nitro and cyano, $R^{10}$, $R^{11}$, $R^{12}$ and $R^{13}$ particularly preferably independently of one another represent hydrogen, methyl, ethyl, n-propyl, isopropyl, n-butyl, isobutyl, s-butyl or t-butyl, $R^{10}$, $R^{11}$, $R^{12}$ and $R^{13}$ very particularly preferably represent hydrogen, m represents 1, 2, 3 or 4, m preferably represents 1 or 2, $R^{14}$ represents an inorganic or organic anion, $R^{14}$ preferably represents bicarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate, citrate or oxalate, $R^{14}$ particularly preferably represents lactate, sulphate, monohydrogenphosphate, dihydrogenphosphate, nitrate, thiosulphate, thiocyanate, citrate, oxalate or formate, $R^{14}$ very particularly preferably represents sulphate.

The ammonium salts and phosphonium salts of the formula (XXIV) can be used in a wide concentration range for increasing the effect of crop protection compositions comprising compounds of the formula (I). In general, the ammonium salts or phosphonium salts are used in the ready-to-use crop protection composition in a concentration of from 0.5 to 80 mmol/l, preferably 0.75 to 37.5 mmol/l, particularly preferably 1.5 to 25 mmol/l. In the case of a formulated product, the concentration of ammonium salt and/or phosphonium salt in the formulation is selected such that it is within these stated general, preferred or particularly preferred ranges following dilution of the formulation to the desired active compound concentration. The concentration of the salt in the formulation here is usually 1-50% by weight.

In one preferred embodiment of the invention, it is not an ammonium salt and/or phosphonium salt, but a penetrant, that is added to the crop protection compositions to increase the activity. An activity increase can be observed even in these cases. The present invention thus also provides the use of a penetrant, and also the use of a combination of penetrant and ammonium salts and/or phosphonium salts for increasing the activity of crop protection compositions which comprise acaricidally/insecticidally active compounds of the formula (I) as active compound. Finally, the invention also provides the use of these compositions for controlling harmful insects.

Suitable penetrants in the present context are all those substances which are usually used for improving the penetration of agrochemical active compounds into plants. Penetrants are defined in this context by their ability to penetrate from the aqueous spray liquor and/or from the spray coating into the cuticle of the plant and thereby increase the mobility of active compounds in the cuticle. The method described in the literature (Baur et al., 1997, *Pesticide Science* 51, 131-152) can be used for determining this property.

Suitable penetrants are, for example, alkanol alkoxylates. Penetrants according to the invention are alkanol alkoxylates of the formula $$R\text{—}O\text{-}(\text{-}AO\text{—})_v\text{—}R' \tag{XXV}$$

in which
R represents straight-chain or branched alkyl having 4 to 20 carbon atoms
R' represents hydrogen, methyl, ethyl, n-propyl, isopropyl, n-butyl, isobutyl, tert-butyl, n-pentyl or n-hexyl,
AO represents an ethylene oxide radical, a propylene oxide radical, a butylene oxide radical or represents mixtures of ethylene oxide and propylene oxide radicals or butylene oxide radicals and
v represents a number from 2 to 30.

A preferred group of penetrants are alkanol alkoxylates of the formula $$R\text{—}O\text{-}(\text{-}EO\text{—})_n\text{-}R' \tag{XXV-a}$$

in which
R has the meaning given above,
R' has the meaning given above,
EO represents —CH2—CH2—O— and
n represents a number from 2 to 20.

A further preferred group of penetrants are alkanol alkoxylates of the formula $$R\text{—}O\text{-}(\text{-}EO\text{—})_p\text{-}(\text{—}PO\text{—})_q\text{-}R' \tag{XXV-b}$$

in which
R has the meaning given above,
R' has the meaning given above,
EO represents —CH2—CH2—O—,
PO represents

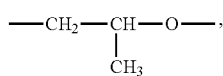

p represents a number from 1 to 10 and
q represents a number from 1 to 10.

A further preferred group of penetrants are alkanol alkoxylates of the formula $$R\text{—}O\text{-}(\text{—}PO\text{—})_r\text{-}(EO\text{—})_s\text{-}R' \tag{XXV-c}$$

in which
R has the meaning given above,
R' has the meaning given above,
EO represents —CH2—CH2—O—,
PO represents

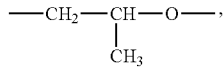

r represents a number from 1 to 10 and
s represents a number from 1 to 10.

A further preferred group of penetrants are alkanol alkoxylates of the formula $$R\text{—}O\text{-}(\text{-}EO\text{—})_p\text{-}(\text{-}BO\text{—})_q\text{-}R' \tag{XXV-d}$$

in which
R and R' have the meanings given above,
EO represents —CH2—CH2—O—,
BO represents

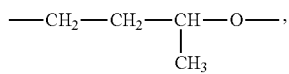

p represents a number from 1 to 10 and
q represents a number from 1 to 10.

A further preferred group of penetrants are alkanol alkoxylates of the formula $$R\text{—}O\text{-}(\text{-}BO\text{—})_r\text{-}(\text{-}EO\text{—})_s\text{-}R' \tag{XXV-e}$$

in which
R and R' have the meanings given above,
BO represents

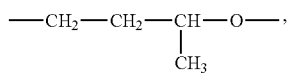

EO represents —CH2—CH2—O—,
r represents a number from 1 to 10 and
s represents a number from 1 to 10.

A further preferred group of penetrants are alkanol alkoxylates of the formula

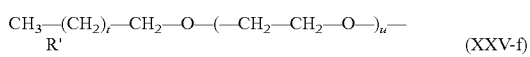

(XXV-f)

in which
R' has the meaning given above,
t represents a number from 8 to 13.
y represents a number from 6 to 17.

In the formulae given above,
R preferably represents butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (XXV-c), mention may be made of 2-ethylhexyl alkoxylate of the formula

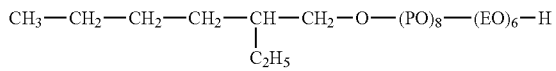
(XXV-c-1)

in which
EO represents —CH2—CH2—O—,
PO represents

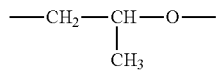

and
the numbers 8 and 6 represent average values.
As an example of an alkanol alkoxylate of the formula (XII-d), mention may be made of the formula CH$_3$—(CH$_2$)$_{10}$—O-(-EO—)$_6$-(-BO—)$_2$-CH$_3$ (XXV-d-1)

in which
EO represents —CH2—CH2—O—,
BO represents

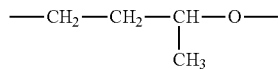

and
the numbers 10, 6 and 2 represent average values.
Particularly preferred alkanol alkoxylates of the formula (XXV-f) are compounds of this formula in which
t represents a number from 9 to 12 and
u represents a number from 7 to 9.
With very particular preference, mention may be made of alkanol alkoxylate of the formula (XXV-f-1)

CH$_3$—(CH$_2$)$_t$—CH$_2$—O—(—CH$_2$—CH$_2$—O—))$_u$-R' (XXV-f-1)

in which
t represents the average value 10.5 and
u represents the average value 8.4.
The above formulae provide general definitions of the alkanol alkoxylates. These substances are mixtures of substances of the stated type with different chain lengths. The indices are therefore average values which may also deviate from whole numbers.

The alkanol alkoxylates of the stated formulae are known, and some of them are commercially available or can be prepared by known methods (cf. WO 98/35 553, WO 00/35 278 and EP-A 0 681 865)

Suitable penetrants also include, for example, substances which promote the solubility of the compounds of the formula (I) in the spray coating. These include, for example, mineral and vegetable oils. Suitable oils are all mineral or vegetable oils—modified or otherwise—which can usually be used in agrochemical compositions. By way of example, mention may be made of sunflower oil, rapeseed oil, olive oil, castor oil, colza oil, maize seed oil, cottonseed oil and soybean oil or the esters of said oils. Preference is given to rapeseed oil, sunflower oil and their methyl or ethyl esters.

The concentration of penetrant can be varied within a wide range. In the case of a formulated crop protection composition, it is generally 1 to 95% by weight, preferably 1 to 55% by weight, particularly preferably 15-40% by weight. In the ready-to-use compositions (spray liquors), the concentrations are generally between 0.1 and 10 g/l, preferably between 0.5 and 5 g/l.

Inventively emphasized combinations of active compound, salt and penetrant are listed in the table below. Here, "according to test" means that any compound which acts as penetrant in the cuticle penetration test (Baur et al., 1997, *Pesticide Science* 51, 131-152) is suitable.

| # | Active compound | Salt | Penetrant |
|---|---|---|---|
| 1 | I | ammonium sulphate | according to test |
| 2 | I | ammonium lactate | according to test |
| 3 | I | ammonium nitrate | according to test |
| 4 | I | ammonium thiosulphate | according to test |
| 5 | I | ammonium thiocyanate | according to test |
| 6 | I | ammonium citrate | according to test |
| 7 | I | ammonium oxalate | according to test |
| 8 | I | ammonium formate | according to test |
| 9 | I | ammonium hydrogenphosphate | according to test |
| 10 | I | ammonium dihydrogenphosphate | according to test |
| 11 | I | ammonium carbonate | according to test |
| 12 | I | ammonium benzoate | according to test |
| 13 | I | ammonium sulphite | according to test |
| 14 | I | ammonium benzoate | according to test |
| 15 | I | ammonium hydrogenoxalate | according to test |
| 16 | I | ammonium hydrogencitrate | according to test |
| 17 | I | ammonium acetate | according to test |
| 18 | I | tetramethylammonium sulphate | according to test |
| 19 | I | tetramethylammonium lactate | according to test |
| 20 | I | tetramethylammonium nitrate | according to test |
| 21 | I | tetramethylammonium thiosulphate | according to test |
| 22 | I | tetramethylammonium thiocyanate | according to test |
| 23 | I | tetramethylammonium citrate | according to test |
| 24 | I | tetramethylammonium oxalate | according to test |
| 25 | I | tetramethylammonium formate | according to test |
| 26 | I | tetramethylammonium hydrogenphosphate | according to test |
| 27 | I | tetramethylammonium dihydrogenphosphate | according to test |
| 28 | I | tetraethylammonium sulphate | according to test |
| 29 | I | tetraethylammonium lactate | according to test |
| 30 | I | tetraethylammonium nitrate | according to test |
| 31 | I | tetraethylammonium thiosulphate | according to test |
| 32 | I | tetraethylammonium thiocyanate | according to test |
| 33 | I | tetraethylammonium citrate | according to test |
| 34 | I | tetraethylammonium oxalate | according to test |
| 35 | I | tetraethylammonium formate | according to test |
| 36 | I | tetraethylammonium hydrogenphosphate | according to test |
| 37 | I | tetraethylammonium dihydrogenphosphate | according to test |

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be used as intermediates or precursors for the synthesis of other active compounds.

The active compounds can be converted into the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

These formulations are produced in a known manner, for example by mixing the active compounds with extenders, i.e. liquid solvents, and/or solid carriers, optionally with the use of surfactants, i.e. emulsifiers and/or dispersants, and/or foam formers. The formulations are produced either in suitable plants or else before or during application.

Suitable for use as auxiliaries are substances which are suitable for imparting to the composition itself and/or to preparations derived therefrom (for example spray liquors, seed dressings) particular properties such as certain technical properties and/or also particular biological properties. Typical auxiliaries include: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligomers or polymers, for example those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Other possible additives are perfumes, mineral or vegetable oils which are optionally modified, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability, may also be present.

The formulations generally comprise between 0.01 and 98% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the inventive active compounds may also be present in their commercially available formulations and in the use forms, prepared from these formulations, as a mixture with synergists. Synergists are compounds which enhance the action of the active compounds, without any need for the synergist added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations may vary within wide limits. The active compound concentration of the application forms may be from 0.00000001 to 95% by weight of active compound, preferably between 0.00001 and 1% by weight.

The compounds are employed in a customary manner appropriate for the use forms.

All plants and plant parts can be treated in accordance with the invention. Plants are understood here to mean all plants and plant populations, such as desired and undesired wild plants or crop plants (including naturally occurring crop plants). Crop plants can thus be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and vegetative and generative propagation material, for example cuttings, tubers, rhizomes, slips and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts in accordance with the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are each commercially available or in use are treated in accordance with the invention. Plant cultivars are to be understood as meaning plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the inventive treatment may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processibility of the harvested products, which exceed the effects normally to be expected.

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other types of vegetable, cotton, tobacco, oilseed rape and also fruit plants (with the fruits apples, pears, citrus fruits and grapes), with particular emphasis being given to maize, soy beans, potatoes, cotton, tobacco and oilseed rape. Traits that are emphasized in particular are increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the improved defence of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal compounds, for example imidazolinones, sulphonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soy bean varieties which are sold under the trade names Roundup Ready® (tolerance against glyphosate, for example maize, cotton, soy beans), Liberty Link® (tolerance against phosphinothricin, for example oilseed rape), IMI® (tolerance against imidazolinones) and STS® (tolerance against sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars which have these genetic traits or genetic traits which are still to be developed and will be developed and/or marketed in the future.

The plants stated can be treated particularly advantageously in accordance with the invention with the compounds of the general formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

from the order of the Heteropterida, for example *Cimex* spp., *Triatoma* spp., *Rhodnius* spp., *Panstrongylus* spp.

From the order of the Blattarida, for example *Blatta orientalis, Periplaneta americana, Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The inventive active compounds of the formula (I) are also suitable for controlling arthropods which attack agricultural livestock, for example cattle, sheep, goats, horses, pigs, donkeys, camels, buffaloes, rabbits, chickens, turkeys, ducks, geese, honey-bees, other domestic animals such as, for example, dogs, cats, caged birds, aquarium fish, and experimental animals, for example hamsters, guinea pigs, rats and mice. The control of these arthropods is intended to reduce cases of death and reduced productivity (of meat, milk, wool, hides, eggs, honey etc.), and so more economic and easier animal husbandry is possible by use of the inventive active compounds.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of 1 to 80% by weight, either directly or after 100- to 10,000-fold dilution, or they may be used as a chemical bath.

It has also been found that the inventive compounds have strong insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus*;

dermapterans, such as *Sirex juvencus, Urocerus gigas, Urocerus gigas taignus, Urocerus augur*;

termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus*;

bristletails, such as *Lepisma saccarina*.

Industrial materials in the present connection are understood to mean inanimate materials, such as preferably plastics, adhesives, sizes, papers and cards, leather, wood, processed wood products and coating compositions.

The ready-to-use compositions may optionally also comprise other insecticides, and optionally one or more fungicides.

With respect to possible additional partners for mixing, reference is made to the insecticides and fungicides mentioned above.

Moreover, the compounds according to the invention can be employed for protecting objects which come into contact with saltwater or brackish water, in particular hulls, screens, nets, buildings, moorings and signalling systems, against fouling.

Furthermore, the compounds according to the invention can be used alone or in combinations with other active compounds as antifouling compositions.

The active compounds are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active compounds and auxiliaries in domestic insecticide products. They are effective against sensitive and resistant species, and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Avicularidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Description of the Preparation Processes and Intermediates

Anilines of the formula (II) are known (e.g. WO2007/043677, WO2008/126858, WO2008/126933) or can be prepared by known methods.

Synthesis of Carboxylic Acids of the Formula (IV-1)

Example No. (IX)

Synthesis of ethyl 2-(bromomethyl)-4-(2-chlorophenyl)pyrimidine-5-carboxylate 820 mg (2.96 mmol) of ethyl 4-(2-chlorophenyl)-2-methylpyrimidine-5-carboxylate and 633 mg (3.55 mmol) of N-bromosuccinimide were dissolved in 18 ml of carbon tetrachloride and, with stirring, heated to the boil. At boiling point, 49 mg (0.29 mmol) of 2,2'-azobis-2-methylpropionitrile were added a little at a time over a period of 5 hours, followed by refluxing for a further hour. After cooling to room temperature, the reaction solution was filtered and the mother liquor was freed from the solvent under reduced pressure. The desired product was isolated by chromatographic purification.

(logP: 3.32; MH$^+$: 357; $^1$H-NMR (400 MHz, DMSO, ppm): 1.00 (t, 3H), 4.12 (q, 2H), 4.80 (s, 2H), 7.50 (m, 4H), 9.30 (s, 1H).

Example No. (X)

Synthesis of ethyl 4-(2-chlorophenyl)-2-[5-(trifluoromethyl)-2H-tetrazol-2-yl]methylpyrimidine-5-carboxylate 345 mg (0.97 mmol) of ethyl 2-(bromomethyl)-4-(2-chlorophenyl)pyrimidine-5-carboxylate were added to a solution of 200 mg (1.45 mmol) of trifluoromethyltetrazole in 10 ml of acetonitrile. Then 174 mg (1.26 mmol) of potassium carbonate were added to the reaction solution, and the mixture was stirred at 60° C. for 6 hours. After cooling to room temperature, the reaction solution was filtered and the mother liquor was freed from the solvent under reduced pressure. 10 ml of water were added to the residue and the mixture was extracted with ethyl acetate (3×20 ml). The combined organic phases were dried over sodium sulphate. The solvent was removed under reduced pressure and the residue was purified by chromatography. (logP: 3.56; MH$^+$: 413; $^1$H-NMR (400 MHz, DMSO, ppm): 0.99 (t, 3H), 4.13 (q, 2H), 6.62 (s, 2H), 7.50 (m, 4H), 9.28 (s, 1H).

Example No. (IV-1)

Synthesis of 4-(2-chlorophenyl)-2-[5-(trifluoromethyl)-2H-tetrazol-2-yl]methylpyrimidine-5-carboxylic acid 1.74 g (4.21 mmol) of ethyl 4-(2-chlorophenyl)-2-{[5-(trifluoromethyl)-2H-tetrazol-2-yl]methyl}pyrimidine-5-carboxylate were dissolved in 12 ml of ethanol and 45% strength aqueous sodium hydroxide solution (5.05 mmol) was added dropwise at 0° C. The reaction was stirred for a further hour and warmed to RT. The ethanol was then removed under reduced pressure, and ice-water (10 ml) was added to the residue. The aqueous phase was extracted with ethyl acetate. The organic phase was discarded. Then the aqueous phase was adjusted to a pH of 3 using hydrochloric acid, and again extracted with ethyl acetate (3×20 ml). The combined organic phases were dried over sodium sulphate. (logP: 2.50; MH$^+$: 385; $^1$H-NMR (400 MHz, DMSO, ppm): 6.59 (s, 2H), 7.48 (m, 4H), 9.27 (s, 1H).

Synthesis of carboxylic acids of the formula IV-2

Example No. XII

Synthesis of methyl 2-(bromomethyl)-4-(2-chlorophenyl)-1,3-thiazole-5-carboxylate 5.00 g (18.6 mmol) of methyl 4-(2-chlorophenyl)-2-methyl-1,3-thiazole-5-carboxylate and 3.38 g (19.0 mmol) of N-bromosuccinimide were dissolved in 100 ml of carbon tetrachloride and, with stirring, heated to the boil. At boiling point, 170 mg (1.00 mmol) of 2,2'-azobis-2-methylpropionitrile were added a little at a time over a period of 5 hours, followed by refluxing for a further hour. After cooling to room temperature, the reaction solution was filtered and the mother liquor was freed from the solvent under reduced pressure. The desired product was isolated by chromatographic purification.

(logP: 4.12; MH$^+$: 345; $^1$H-NMR (400 MHz, DMSO, ppm): 3.70 (s, 3H), 5.76 (s, 2H), 7.40-7.60 (m, 4H).

Example No. XIII

Synthesis of methyl 4-(2-chlorophenyl)-2-{[5-(trifluoromethyl)-2H-tetrazol-2-yl]methyl}-1,3-thiazole-5-carboxylate 5.00 g (14.4 mmol) of methyl 2-(bromomethyl)-4-(2-chlorophenyl)-1,3-thiazole-5-carboxylate were added to a solution of 10.00 g (18.7 mmol) of trifluoromethyltetrazole sodium salt in 100 ml of acetonitrile. Then 600 mg (4.32 mmol) of potassium carbonate were added to the reaction solution, and the mixture was stirred at 60° C. for 6 hours. After cooling to room temperature, the reaction solution was filtered and the mother liquor was freed from the solvent under reduced pressure. 10 ml of water were added to the residue and the mixture was extracted with ethyl acetate (3×20 ml). The combined organic phases were dried over sodium sulphate. The solvent was removed under reduced pressure and the residue was purified by chromatography.
(logP: 3.60; MH$^+$: 404; $^1$H-NMR (400 MHz, DMSO, ppm): 3.71 (s, 3H), 6.70 (s, 2H), 7.40-7.60 (m, 4H).

Example No. X (IV-2)

Synthesis of 4-(2-chlorophenyl)-2-{[5-(trifluoromethyl)-2H-tetrazol-2-yl]methyl}-1,3-thiazole-5-carboxylic acid 3.60 g (8.91 mmol) of methyl 4-(2-chlorophenyl)-2-{[5-(trifluoromethyl)-2H-tetrazol-2-yl]methyl}-1,3-thiazole-5-carboxylate were dissolved in 18 ml of dioxane and 6 ml of water and 45% strength aqueous sodium hydroxide solution (10.06 mmol) was added dropwise at 0° C. The reaction was stirred for a further hour and warmed to RT. The ethanol was then removed under reduced pressure, and ice-water (10 ml) was added to the residue. The aqueous phase was extracted with ethyl acetate. The organic phase was discarded. Then the aqueous phase was adjusted to a pH of 3 using hydrochloric acid, and again extracted with ethyl acetate (3×20 ml). The combined organic phases were dried over sodium sulphate.
(logP: 2.63; MH$^+$: 390; $^1$H-NMR (400 MHz, DMSO, ppm): 6.65 (s, 2H), 7.36-7.55 (m, 4H).

Synthesis of carboxylic acids of the formula IV-3

Example No. XV

Synthesis of methyl 4-acetyl-1-(3-chloropyridin-2-yl)-1H-pyrrole-2-carboxylate

Under argon, 5.0 g (15.6 mmol) of methyl 4-bromo-1-(3-chloropyridin-2-yl)-1H-pyrrole-2-carboxylate were dissolved in THF, and 8.2 g (21.9 mmol) of (1-ethoxyvinyl)tributylstannane, 2.1 g of lithium chloride and 0.9 g (0.8 mmol) of tetrakis(triphenylphosphine)palladium were added at room temperature and the mixture was stirred under reflux for 48 h. The solvent was then distilled off, and the residue was taken up in 200 ml of THF and stirred in the presence of 12 ml of 2N hydrochloric acid at RT for a further 24 h. Once more, the solvent was distilled off, and the residue was dissolved in 120 ml of methyl tert-butyl ether and, at RT, stirred vigorously with 120 ml of saturated potassium fluoride solution for 1 h. The organic phase was separated off and concentrated. The desired product was isolated by chromatographic purification.

(logP: 1.74; MH$^+$: 279; $^1$H-NMR (400 MHz, DMSO, ppm): 2.42 (s, 3H), 3.66 (s, 3H), 7.63-7.66 (m, 1H), 8.12 (s, 1H), 8.21 (d, 1H), 8.54 (d, 1H).

Example No. XVI

Synthesis of methyl 4-(bromoacetyl)-1-(3-chloropyridin-2-yl)-1H-pyrrole-2-carboxylate 427 mg (1.48 mmol) of methyl 4-acetyl-1-(3-chloropyridin-2-yl)-1H-pyrrole-2-carboxylate were initially charged in 12 ml of dioxane, and 284 mg (1.78 mmol) of bromine were added dropwise at RT. The mixture was then stirred under reflux for 7 h. The solvent was distilled off under reduced pressure, giving an oil which was directly, without purification, reacted further.

(logP: 2.28; MH$^+$: 358)

Example No. XVII

Synthesis of methyl 1-(3-chloropyridin-2-yl)-4-{[5-(trifluoromethyl)-2H-tetrazol-2-yl]acetyl}-1H-pyrrole-2-carboxylate 890 mg (1.61 mmol) of 5-(trifluoromethyl)-2H-tetrazole and 297 mg (2.14 mmol) of potassium carbonate were initially charged in 10 ml of acetonitrile and heated at reflux for 15 min. 630 mg (1.07 mmol) of methyl 4-(bromoacetyl)-1-(3-chloropyridin-2-yl)-1H-pyrrole-2-carboxylate, dissolved in 10 ml of acetonitrile, were added, and the reaction mixture was stirred at 70° C. for 1 h. The solvent was distilled off, the residue was taken up in water and the mixture was extracted twice with dichloromethane. The combined organic phases are washed with sodium chloride solution, dried over sodium sulphate and concentrated. The desired product was isolated by chromatographic purification.

(logP: 2.97; MH$^+$: 415; $^1$H-NMR (400 MHz, DMSO, ppm): 3.69 (s, 3H), 6.65 (s, 2H), 7.57 (s, 1H), 7.67-7.70 (m, 1H), 8.25 (d, 1H), 8.36 (s, 1H), 8.57 (d, 1H).

Example No. IV-3

Synthesis of 1-(3-chloropyridin-2-yl)-4-{[5-(trifluoromethyl)-2H-tetrazol-2-yl]acetyl}-1H-pyrrole-2-carboxylic acid 130 mg (0.31 mmol) of methyl 1-(3-chloropyridin-2-yl)-4-{[5-(trifluoromethyl)-2H-tetrazol-2-yl]acetyl}-1H-pyrrole-2-carboxylate were dissolved in 3 ml of ethanol, 19 mg (0.47 mmol) of 2N aqueous sodium hydroxide solution were added and the mixture was stirred at RT for 4 h. The solvent was distilled off under reduced pressure, the residue was taken up in water and the mixture was extracted once with methyl tert-butyl ether. The aqueous phase was then acidified with 2N hydrochloric acid and extracted three times with ethyl acetate. The combined organic phases were dried over sodium sulphate and concentrated.

(logP: 2.24; MH$^+$: 401)

Preparation Examples

The preparation processes described above can be used to give the compounds of the formula (I)— for example the following compounds of the formula (I):

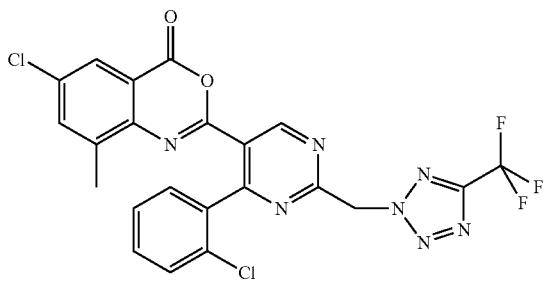 [SMILES: Cc1cc(Cl)cc2c(=O)oc(-c3cnc(Cn4nnc(C(F)(F)F)n4)nc3-c3ccccc3Cl)nc12]

Synthesis of 6-chloro-2-[4-(2-chlorophenyl)-2-{[5-(trifluoromethyl)-2H-tetrazol-2-yl]methyl}pyrimidin-5-yl]-8-methyl-4H-3,1-benzoxazin-4-one At RT, 385 mg (1.30 mmol) of 4-(2-chlorophenyl)-2-{[5-(trifluoromethyl)-2H-tetrazol-2-yl]methyl}pyrimidine-5-carboxylic acid was initially charged in 5 ml of acetonitrile, and 0.27 ml (2.33 mmol) of lutidine was added. With stirring, the solution was then cooled to 0° C., 0.14 ml (1.78 mmol) of methanesulphonyl chloride, dissolved in 2 ml of acetonitrile, was added dropwise and the mixture was stirred at 0° C. for another 15 min. A little at a time, an acetonitrile suspension (3 ml) of 0.53 ml (4.54 mmol) of lutidine and 289 mg (1.56 mmol) of 2-amino-5-chloro-3-methylbenzoic acid was then added to this reaction mixture, and stirring was continued for another 15 min. 0.14 ml (1.78 mmol) of methanesulphonyl chloride, dissolved in 2 ml of acetonitrile, was then added dropwise. The reaction was stirred overnight, with the temperature increasing to RT. The solvent was removed under reduced pressure. The residue was then poured into ice-water and mixed in an ultrasonic bath. The residue was filtered off, again taken up in water and sonicated once more. The residue is filtered off, washed with water and dried under reduced pressure. 708 mg (88% of theory; content 86%) of the desired product were isolated. There was not further purification.

logP: 5.16; MH$^+$: 534; $^1$H-NMR (400 MHz, DMSO-d$_6$, δ, ppm): 1.96 (s, 3H), 6.67 (s, 2H), 7.40-7.55 (m, 5H), 7.83 (m, 1H), 7.94 (m, 1H).

Synthesis of N-[4-chloro-2-methyl-6-(methylcarbamoyl)phenyl]-4-(2-chlorophenyl)-2-{[5-(trifluoromethyl)-2H-tetrazol-2-yl]methyl}pyrimidine-5-carboxamide

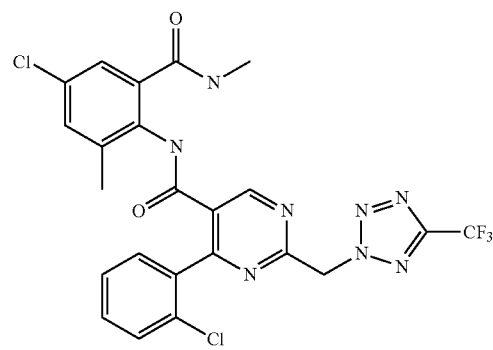 [SMILES: CNC(=O)c1cc(Cl)cc(C)c1NC(=O)c1cnc(Cn2nnc(C(F)(F)F)n2)nc1-c1ccccc1Cl]

100 mg (0.18 mmol) of 6-chloro-2-[4-(2-chlorophenyl)-2-{[5-(trifluoromethyl)-2H-tetrazol-2-yl]methyl}pyrimidin-5-yl]-8-methyl-4H-3,1-benzoxazin-4-one were initially charged in 3 ml of THF, and 0.234 ml (0.46 mmol) of a 2 molar methylamine/THF solution was added at RT. The reaction mixture was then stirred at 45° C. for 15 min. After cooling, the mixture was concentrated and purified chromatographically on silice gel using cyclohexane/ethyl acetate. 48 mg (40% of theory; content 89%) of the desired product were isolated.

logP: 3.13; MH$^+$: 566; $^1$H-NMR (400 MHz, DMSO-d$_6$, δ, ppm): 2.05 (s, 3H), 2.69 (m, 3H), 6.60 (s, 2H), 7.35 (s, 1H), 7.40-7.55 (m, 4H), 8.32 (m, 1H); 9.13 (s, 1H).

The examples below can be obtained in an analogous manner, some of the compounds of the formula (I) being present as regioisomers. With respect to the NMR data, the table below states the chemical shifts and the corresponding signal intensities; for example, for compound 1:

Signal 1:
10.272; 4.21; for 10.272 ppm (chemical shift), 4.21 (signal intensity);

Signal 2:
9.899; 0.35; for 9.899 ppm (chemical shift), 0.35 (signal intensity);

| No. | Structure | log P | MH+ | NMR |
|---|---|---|---|---|
| 1 | ![structure] | 3.98 | 614 | (10.272;4.21),(9.899;0.35),(8.370;1.46),(8.360;1.45),(8.350;0.70),(7.642;0.44),(7.639;0.40),(7.637;0.39),(7.562;4.89),(7.542;3.41),(7.540;3.35),(7.528;2.10),(7.524;2.29),(7.510;3.13),(7.505;3.62),(7.499;4.18),(7.494;3.45),(7.479;1.98),(7.474;1.78),(7.460;3.04),(7.455;2.54),(7.440;1.89),(7.435;1.71),(7.407;2.18),(7.404;2.16),(7.388;2.82),(7.385;2.65),(7.369;1.06),(7.366;1.01),(7.301;0.39),(6.706;12.44),(6.644;0.87),(6.598;0.53),(6.468;0.58),(4.040;0.62),(4.022;0.60),(3.380;0.46),(3.358;0.75),(3.321;2.64),(3.288;1167.97),(3.252;1.33),(3.228;0.60),(3.202;0.40),(2.890;0.35),(2.732;0.45),(2.695;0.57),(2.672;1.90),(2.668;2.41),(2.654;10.21),(2.642;10.01),(2.605;0.96),(2.593;0.96),(2.538;8.56),(2.521;7.60),(2.508;108.05),(2.503;210.37),(2.499;278.91),(2.494;197.59),(2.490;92.86),(2.407;0.65),(2.330;1.35),(2.326;1.84),(2.321;1.30),(2.316;0.73),(2.210;0.77),(2.158;1.30),(2.114;15.00),(2.095;1.07),(2.067;2.47),(2.049;1.34),(1.986;2.65),(1.962;1.18),(1.293;0.71),(1.237;0.87),(1.193;0.77),(1.175;1.48),(1.157;0.87),(0.008;1.54),(−0.000;32.01),(−0.009;1.13) |

-continued
| No. | Structure | log P | MH+ | NMR |
|---|---|---|---|---|
| 2 | 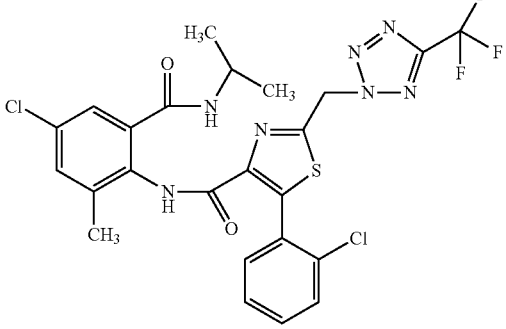 | 4.34 | 598 | (10.088;0.36),(8.190;1.14),(8.177;1.17),(7.554;1.44), (7.552;1.53),(7.541;1.84),(7.539;1.81),(7.512;124), (7.509;1.42),(7.499;1.65),(7.497;1.80),(7.471;0.93), (7.468;1.02),(7.458;1.54),(7.456;1.40),(7.445;1.14), (7.442;1.03),(7.435;1.75),(7.434;1.76),(7.431;2.03), (7.430;1.87),(7.401;1.25),(7.399;124),(7.396;0.35), (7.389;1.88),(7.386;1.84),(7.376;0.82),(7.374;0.82), (7.323;1.98),(7.319;1.92),(6.705;7.83),(6.619;0.95), (6.476;0.44),(3.887;0.52),(3.876;0.77),(3.863;0.75), (3.852;0.51),(3.344;455.59),(3.325;0.59),(3.320;0.58), (3.318;0.49),(2.884;1.07),(2.618;0.59),(2.615;0.85), (2.612;0.60),(2.542;4.85),(2.524;1.47),(2.521;1.89), (2.518;1.74),(2.509;44.47),(2.506;100.07),(2.503;137.84), (2.500;99.26),(2.497;44.89),(2.405;0.38),(2.390;0.64), (2.387;0.92),(2.384;0.66),(2.216;0.58),(2.153;0.45), (2.122;9.53),(2.102;0.72),(2.097;0.77),(2.077;1.50), (2.053;0.73),(1.918;0.43),(1.397;12.10),(1.292;0.37), (1.113;1.01),(1.102;1.00),(1.087;1.54),(1.076;1.58), (1.061;0.98),(1.051;0.98),(0.977;1.01),(0.966;13.50), (0.955;12.69),(0.005;0.81) |
| 3 | 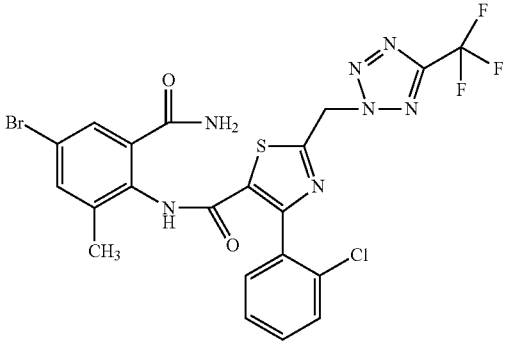 | 3.45 | 601 | (9.988;2.73),(9.866;0.46),(7.879;1.50),(7.715;0.51), (7.710;0.49),(7.617;0.56),(7.576;3.08),(7.546;4.65), (7.541;3.66),(7.522;2.60),(7.517;2.94),(7.502;4.98), (7.498;5.10),(7.490;3.56),(7.454;1.56),(7.449;1.89), (7.436;3.17),(7.431;2.65),(7.417;3.88),(7.412;3.31), (7.398; 1.92),(7.378;0.82),(7.301;0.48),(7.026;0.62), (7.005;0.54),(6.871;0.57),(6.718;0.65),(6.675;10.68), (6.628;0.48),(6.263;0.49),(5.742;8.23),(3.602;0.48), (3.567;0.54),(3.470;0.45),(3.453;0.55),(3.422;0.64), (3.404;0.74),(3.395;0.95),(3.288;1896.54),(3.265;32.89), (3.228;0.78),(2.907;0.68),(2.695;0.52),(2.672;3.08), (2.668;4.03),(2.663;3.01),(2.639;0.49),(2.627;0.56), (2.615;0.68),(2.597;0.77),(2.566;1.24),(2.538;6.31), (2.521;16.64),(2.508;226.17),(2.503;439.87), (2.499;583.78),(2.494;412.79),(2.490;193.00), (2.405;5.02),(2.335;1.37), (2.330;2.69),(2.326;3.66),(2.321;2.55),(2.204;1.79), (2.183;1.05),(2.102;15.00),(2.067;1.03),(2.048;1.11), (1.997;0.71),(1.986;0.55),(1.907;0.63),(1.357;7.10), (1.246;2.61),(1.238;1.07),(1.175;0.49),(1.091;0.56), (0.891;0.84),(0.008;4.77),(−0.000;96.17),(−0.008;3.25) |
| 4 | 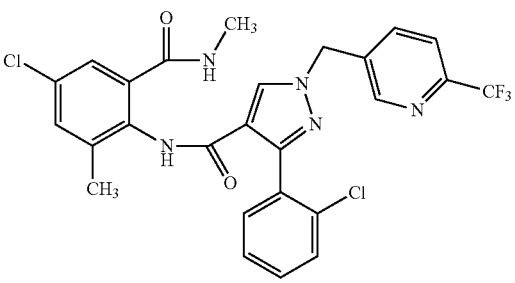 [SMILES: CNC(=O)c1cc(Cl)cc(C)c1NC(=O)c1cn(Cc2ccc(C(F)(F)F)nc2)nc1-c1ccccc1Cl] | 3.12 | 562 | (9.569;3.38),(9.561;2.92),(8.797;2.30),(8.554;2.92), (8.366;2.93),(8.284;1.17),(8.273;1.21),(8.237;2.95), (8.208;1.46),(8.196;1.51),(8.085;1.28),(8.039;1.59), (8.035;1.63),(7.979;3.04),(7.958;1.93),(7.843;2.68), (7.823;3.90),(7.695;1.85),7.672;1.40),(7.543;1.58), (7.523;4.00),(7.513;1.73),(7.505;1.79),(7.498;2.15), (7.491;2.74),(7.478;1.28),(7.471;1.44),(7.459;1.80), (7.454;2.63),(7.441;7.14),(7.439;6.11),(7.423;4.57), (7.415;5.00),(7.408;4.25),(7.398;3.15),(7.380;3.15), (7.374;2.13),(7.361;3.29),(7.356;3.02),(7.343;1.92), (7.335;3.37),(7.329;3.08),(7.321;4.15),(7.315;3.33), (5.654;6.11),(5.311;3.46),(5.282;339),(4.040;3.33), (4.022;3.43),(3.290;1061.61),(2.684;2.12),(2.673;3.55), (2.668;3.02),(2.661;9.01),(2.652;14.18),(2.640;10.86), (2.625;1.79),(2.613;1.67),(2.538;8.76),(2.521;7.47), (2.508;106.42),(2.504;208.63),(2.499;278.27), (2.494;196.94),(2.490;92.43),(2.330;1.36), (2.326;1.80),(2.321;1.34), (2.214;2.59),(2.159;11.81),(2.129;14.91),(2.109;2.80), (2.067;1.20),(2.049;1.49),(1.986;15.00),(1.193;4.21), (1.175;8.33),(1.157;4.16),(0.008;1.13),(−0.000;25.35) |

-continued

| No. | Structure | log P | MH+ | NMR |
|---|---|---|---|---|
| 5 | 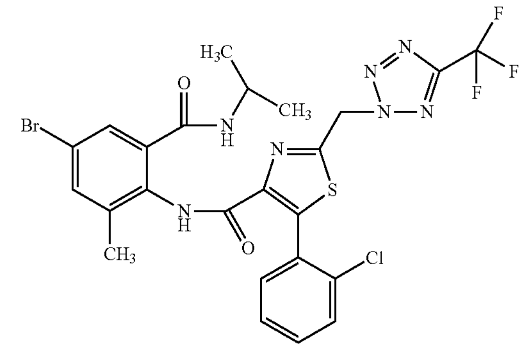 | 4.48 | 642 | (10.061;2.78),(8.151;1.25),(8.131;1.26),(7.548;3.69),(7.530;2.33),(7.527;2.37),(7.509;1.31),(7.504;1.54),(7.489;1.91),(7.485;2.10),(7.474;1.21),(7.470;1.16),(7.455;2.14),(7.451;1.81),(7.441;2.79),(7.436;3.59),(7.431;1.58),(7.403;1.61),(7.399;1.54),(7.384;1.99),(7.380;1.87),(7.365;0.78),(7.362;0.72),(6.688;8.65),(6.462;0.64),(4.039;0.58),(3.899;0.66),(3.882;1.00),(3.866;0.93),(3.847;0.64),(3.398;0.96),(3.366;1.42),(3.353;2.29),(3.293;3174.69),(3.271;32.58),(3.238;2.02),(3.230;1.25),(3.226;1.17),(3.174;0.60),(2.677;1.57),(2.673;3.05),(2.668;4.09),(2.664;3.12),(2.584;0.58),(2.538;6.14),(2.522;16.14),(2.508;233.09),(2.504;458.49),(2.499;613.11),(2.495;434.14),(2.490;204.73),(2.335;1.49),(2.331;3.00),(2.326;3.94),(2.321;2.81),(2.317;139),(2.151;0.57),(2.119;10.71),(2.095;1.00),(2.084;2.33),(2.067;0.88),(2.048;1.09),(1.986;2.32),(1.399;3.01),(1.237;1.16),(1.193;0.75),(1.175;1.74),(1.168;1.76),(1.158;0.98),(1.092;0.93),(1.075;1.09),(1.071;1.31),(1.054;0.99),(0.988;1.84),(0.977;15.00),(0.960;14.64),(0.891;0.85),(0.008;3.19),(−0.000;71.66),(−0.008;2.49) |
| 6 | 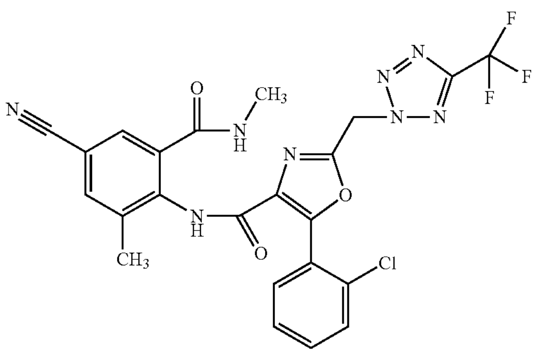 [SMILES: CNC(=O)c1cc(C#N)cc(C)c1NC(=O)c1nc(Cn2nnc(C(F)(F)F)n2)oc1-c1ccccc1Cl] | 3.25 | 545 | (10.589;1.10),(8.533;0.87),(7.865;2.92),(7.830;3.67),(7.825;3.16),(7.804;0.43),(7.665;1.95),(7.661;2.04),(7.646;2.49),(7.642;2.62),(7.620;1.91),(7.618;2.00),(7.600;3.55),(7.597;3.41),(7.585;0.48),(7.575;1.73),(7.571;1.82),(7.557;2.55),(7.553;2.36),(7.537;1.44),(7.532;1.23),(7.478;1.93),(7.475;1.94),(7.459;2.66),(7.456;2.62),(7.440;1.22),(7.437;1.17),(7.430;0.31),(6.625;11.62),(6.532;0.77),(6.358;0.84),(3.387;0.35),(3.376;0.37),(3.357;0.42),(3.290;663.56),(3.271;2.03),(3.256;0.62),(3.249;0.46),(2.858;4.27),(2.743;1.40),(2.731;1.83),(2.721;9.58),(2.709;9.44),(2.695;1.23),(2.683;1.00),(2.673;0.91),(2.668;1.08),(2.664;0.81),(2.591;0.42),(2.582;2.29),(2.570;2.19),(2.554;0.48),(2.538;4.69),(2.522;4.06),(2.508;55.84),(2.504;108.12),(2.499;142.78),(2.495;100.13),(2.490;46.20),(2.331;0.70),(2.326;0.90),(2.322;0.63),(2.275;0.59),(2.222;15.00),(2.209;1.70),(2.132;0.64),(2.099;1.22),(2.067;0.63),(2.049;0.69),(1.986;1.01),(1.293;0.36),(1.238;0.50),(1.193;0.36),(1.175;0.62),(1.158;0.33),(0.008;0.70),(−0.000;14.39),(−0.008;0.42) |
| 7 | 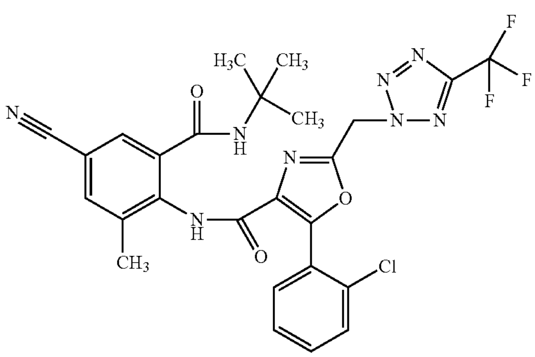 | 3.95 | 587 | (7.824;0.53),(7.725;0.63),(7.658;0.49),(7.655;0.54),(7.639;0.61),(7.635;0.63),(7.612;0.39),(7.595;0.82),(7.592;0.77),(7.576;0.38),(7.573;0.38),(7.558;0.52),(7.554;0.46),(7.478;0.42),(7.474;0.40),(7.459;0.56),(7.456;0.55),(6.624;2.30),(3.289;324.31),(2.914;0.37),(2.673;0.35),(2.668;0.47),(2.664;0.35),(2.538;2.32),(2.521;1.98),(2.508;27.37),(2.503;53.02),(2.499;70.11),(2.494;49.15),(2.490;22.66),(2.330;0.34),(2.326;0.45),(2.321;0.32),(2.229;2.87),(2.091;0.56),(2.067;0.32),(2.049;0.36),(1.399;4.23),(1.368;2.51),(1.265;0.37),(1.258;1.27),(1.211;0.94),(1.198;15.00),(−0.000;4.70) |
| 8 | 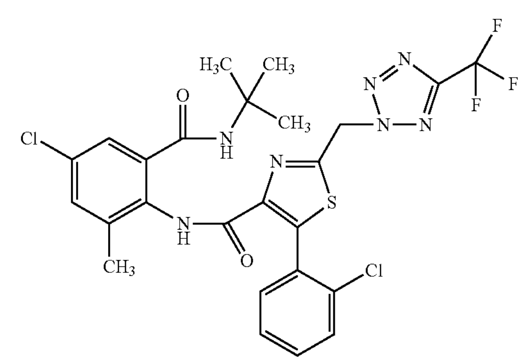 | 4.75 | 612 | (9.857;0.97),(7.722;0.97),(7.552;0.51),(7.550;0.55),(7.533;0.80),(7.530;0.77),(7.523;0.31),(7.502;0.49),(7.498;0.64),(7.484;0.72),(7.479;0.89),(7.472;0.50),(7.458;0.75),(7.453;0.59),(7.438;0.53),(7.433;0.40),(7.407;0.56),(7.403;0.59),(7.396;0.84),(7.388;1.18),(7.385;0.73),(7.250;0.90),(7.244;0.78),(6.675;2.99),(6.643;0.48),(3.292;524.17),(3.269;7.71),(2.673;0.62),(2.668;0.81),(2.664;0.60),(2.659;0.31),(2.538;1.33),(2.521;3.70),(2.508;45.90),(2.504;88.96),(2.499;117.97),(2.495;83.54),(2.490;39.28),(2.330;0.53),(2.326;0.71),(2.321;0.50),(2.208;0.31),(2.157;0.59),(2.121;3.64),(2.067;0.41),(1.903;0.54),(1.399;1.91),(1.301;0.51),(1.285;2.65),(1.258;0.59),(1.237;0.42),(1.136;15.00),(−0.000;0.48) |

-continued

| No. | Structure | log P | MH+ | NMR |
|---|---|---|---|---|
| 9 | 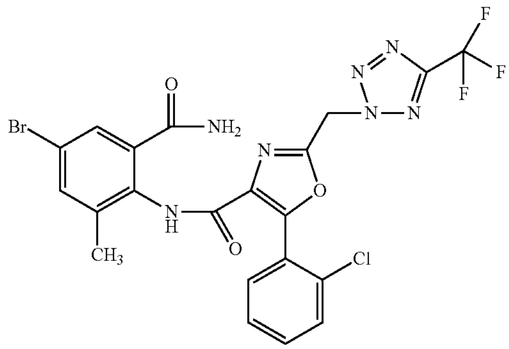 | 3.5 | 568 | (10.358;0.35),(8.002;1.93),(7.722;0.42),(7.718;0.42),(7.656;1.89),(7.654;2.03),(7.644;2.35),(7.641;2.36),(7.636;0.33),(7.632;0.57),(7.628;0.63),(7.617;5.45),(7.616;5.90),(7.613;4.99),(7.604;3.22),(7.602;3.02),(7.595;0.32),(7.592;043),(7.575;3.20),(7.571;2.86),(7.569;2.08),(7.566;1.69),(7.562;0.36),(7.556;2.16),(7.554;2.04),(7.547;0.72),(7.543;1.80),(7.540;1.36),(7.528;0.35),(7.517;0.38),(7.513;0.43),(7.477;1.61),(7.475;1.58),(7.464;2.37),(7.463;2.32),(7.452;1.13),(7.450;1.11),(7.308;0.37),(7.305;0.38),(7.117;1.48),(6.613;10.31),(6.585;0.70),(6.343;0.44),(6.298;0.59),(3.400;0.35),(3.388;0.94),(3.376;1.22),(3.349:385.18),(3.321;0.42),(2.911;0.43),(2.618;0.64),(2.615;0.89),(2.612;0.64),(2.524;1.71),(2.521;2.11),(2.518;2.06),(2.510;47.18),(2.507;102.21),(2.503;141.07),(2.500;102.64),(2.497;47.08),(2.394;0.32),(2.391;0.66),(2.388;0.93),(2.385;0.66),(2.382;0.32),(2.297;10.39),(2.215;0.95),(2.201;2.17),(2.169;13.50),(2.152;0.81),(2.102;2.09),(2.087;0.31),(2.077;0.84),(1.993;0.92),(1.990;0.48),(1.102;0.79),(1.091;1.60) |
| 10 | 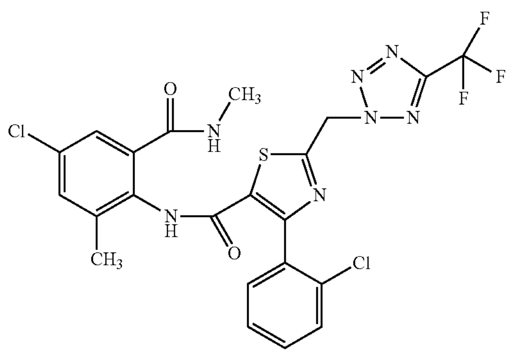 [SMILES: CNC(=O)c1cc(Cl)cc(C)c1NC(=O)c1sc(Cn2nnc(C(F)(F)F)n2)nc1-c1ccccc1Cl] | 3.63 | 570 | (9.987;0.71),(8.380;0.66),(8.372;0.66),(7.572;0.41),(7.569;0.44),(7.541;0.50),(7.519;1.14),(7.506;1.35),(7.501;0.63),(7.492;0.93),(7.489;0.94),(7.480;1.07),(7.477;1.11),(7.459;1.34),(7.455;1.43),(7.447;0.66),(7.444;0.69),(7.434;1.01),(7.431 ;0.94),(7.421;0.74),(7.418;0.66),(7.409;0.87),(7.396;0.93),(7.381;0.51),(7.377;0.37),(7.358;1.43),(7.355;1.37),(6.701;4.07),(3.346;323.35),(3.326;0.50),(3.323;0.53),(2.676;1.48),(2.671;3.58),(2.664;3.41),(2.621;0.33),(2.618;0.61),(2.615;0.84),(2.612;0.60),(2.609;0.30),(2.524;1.37),(2.521;1.75),(2.518;1.70),(2.509;40.48),(2.506;88.93),(2.503;122.93),(2.500;90.02),(2.497;41.16),(2.393;0.31),(2.390;0.63),(2.387;0.85),(2.384;0.73),(2.381;0.59),(2.372;6.77),(2.297;13.50),(2.212;1.02),(2.117;0.86),(2.107;6.31),(2.077;1.04),(1.910;0.28),(−0.000;8.27) |
| 11 | 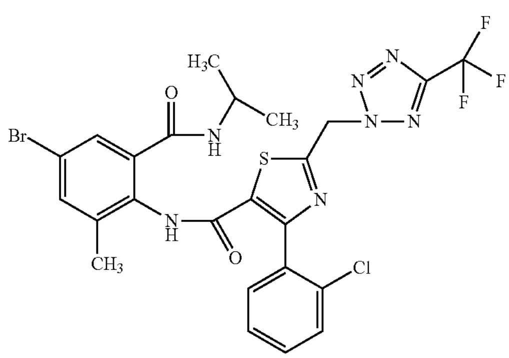 | 4.28 | 642 | (9.797;1.43),(8.189;0.59),(8.170;0.66),(7.697;0.37),(7.650;0.43),(7.610:0.62),(7.594;0.50),(7.556;1.43),(7.518;0.95),(7.515;1.01),(7.498;1.41),(7.496;1.47),(7.465;0.98),(7.456;0.94),(7.450;0.99),(7.441;1.99),(7.437;2.62),(7.418;0.96),(7.412;0.88),(7.407;0.95),(7.389;0.96),(7.368;0.47),(6.684;4.10),(3.940;0.43),(3.923;0.64),(3.906;0.68),(3.890;0.43),(3.394;0.35),(3.292;371.20),(3.170;0.62),(2.695;0.33),(2.672;0.95),(2.668;1.27),(2.664;0.98),(2.538;5.69),(2.521;5.40),(2.508;72.92),(2.503;142.17),(2.499;188.71),(2.494;133.99),(2.490;63.11),(2.330;0.85),(2.326;1.21),(2.321;0.89),(2.294;9.45),(2.212;0.68),(2.100;0.97),(2.072;5.68),(2.067;4.65),(2.048;0.95),(1.818;0.69),(1.293;0.46),(1.237;0.36),(1.179;15.00),(1.163;14.71),(1.099;0.33),(1.091;0.54),(1.069;9.67),(1.052;9.55),(1.040;1.42),(1.018;0.42),(−0.000;20.17),(−0.009;0.74) |
| 12 | 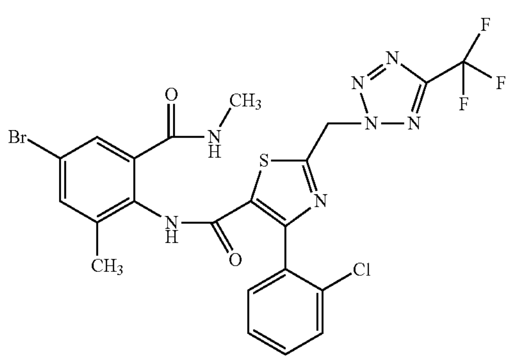 | 3.73 | 614 | (9.929;0.37),(8.322;1.01),(7.674;0.34),(7.612;0.38),(7.602;0.34),(7.573;1.91),(7.515;1.79),(7.495;3.21),(7.473;3.66),(7.451;1.53),(7.446;1.56),(7.432;2.28),(7.427;2.02),(7.408;2.27),(7.390;1.48),(7.368;0.89),(7.297;0.43),(7.284;0.35),(7.263;0.43),(7.233;0.30),(6.682;5.88),(6.490;0.33),(3.445;0.33),(3.432;0.32),(3.382;0.49),(3.368;0.72),(3.288;1183.09),(3.248;1.31),(3.230;0.49),(3.202;0.33),(2.890;1.13),(2.732;1.07),(2.695;1.02),(2.672;6.92),(2.663;6.08),(2.622;0.63),(2.616;0.64),(2.600;0.61),(2.538;9.97),(2.521;8.94),(2.508;122.15),(2.503;238.04),(2.499;316.72),(2.494;224.10),(2.490;105.54),(2.406;0.53),(2.376;15.00),(2.330;1.52),(2.326;2.08),(2.321;1.40),(2.292;11.43),(2.209;0.86),(2.098;7.02),(2.067;6.38),(2.048;1.99),(1.821;0.70),(1.356;0.48),(1.292;0.77),(1.236;0.59),(1.229;0.52),(1.159;0.49),(1.147;0.43),(0.008;1.83),(−0.000;37.58),(−0.009;1.27) |

-continued

| No. | Structure | log P | MH+ | NMR |
|---|---|---|---|---|
| 13 | 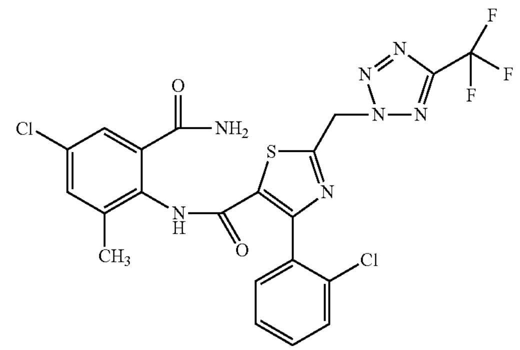 [SMILES: Cc1cc(Cl)cc(C(N)=O)c1NC(=O)c1sc(Cn2nnc(C(F)(F)F)n2)nc1-c1ccccc1Cl] | 3.34 | 556 | (9.989;3.10),(7.871;1.72),(7.542;0.35),(7.522;2.40),(7.518;2.80),(7.503;5.54),(7.499;5.63),(7.449;3.85),(7.444;3.82),(7.436;3.93),(7.431;3.53),(7.424;5.38),(7.418;6.72),(7.412;3.80),(7.399;2.05),(7.382;0.74),(6.677;11.03),(6.629;0.30),(4.507;0.31),(4.057;1.13),(4.040;3.42),(4.022;3.40),(4.004;1.19),(3.353;0.46),(3.347;0.48),(3.286;568.48),(3.244;0.50),(2.673;0.88),(2.668;1.20),(2.663;0.92),(2.538;1.97),(2.521;5.52),(2.508;71.43),(2.503;137.28),(2.499;181.52),(2.494;128.45),(2.490;60.77),(2.405;1.41),(2.330;0.87),(2.326;1.12),(2.321;0.82),(2.107;14.82),(2.067;1.33),(2.048;0.39),(1.986;15.00),(1.237;0.78),(1.193;4.22),(1.175;8.33),(1.157;4.16),(1.143;1.78),(0.008;1.53),(−0.000;30.10),(−0.008;1.13) |
| 14 | 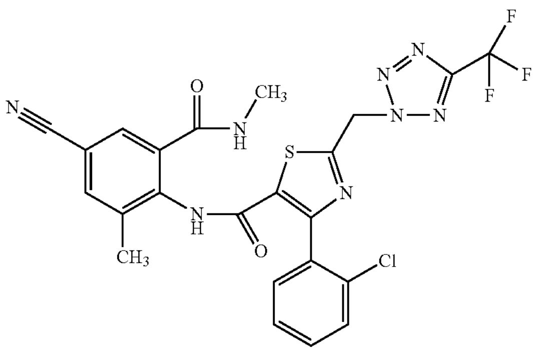 [SMILES: CNC(=O)c1cc(C#N)cc(C)c1NC(=O)c1sc(Cn2nnc(C(F)(F)F)n2)nc1-c1ccccc1Cl] | 3.19 | 561 | (10.260;5.13),(10.169;1.17),(8.436;1.44),(8.399;0.59),(7.995;0.98),(7.894;0.95),(7.831;2.94),(7.800;1.12),(7.796;1.09),(7.765;4.29),(7.533;0.33),(7.514;2.84),(7.495;4.54),(7.473;1.89),(7.451;1.53),(7.446;1.74),(7.432;3.22),(7.427;2.70),(7.413;2.68),(7.408;3.27),(7.387;2.12),(7.369;0.76),(6.958;1.00),(6.689;14.82),(6.634;0.84),(3.515;0.31),(3.403;0.47),(3.337;1.34),(3.286;902.63),(3.248;0.53),(3.239;0.32),(2.857;5.72),(2.747;0.33),(2.697;3.87),(2.685;13.99),(2.673;12.41),(2.634;0.96),(2.622;0.96),(2.582;3.28),(2.569;3.29),(2.538;3.29),(2.521;8.00),(2.508;104.26),(2.503;200.60),(2.499;264.66),(2.494;187.38),(2.490;87.91),(2.330;1.18),(2.326;1.58),(2.321;1.09),(2.277;4.17),(2.182;0.31),(2.143;15.00),(2.132;5.42),(2.115;0.67),(2.067;1.18),(2.049;0.49),(1.986;0.78),(1.259;0.36),(1.238;0.84),(1.175;0.47),(1.143;0.77),(−0.000;31.49),(−0.008;1.13) |
| 15 | 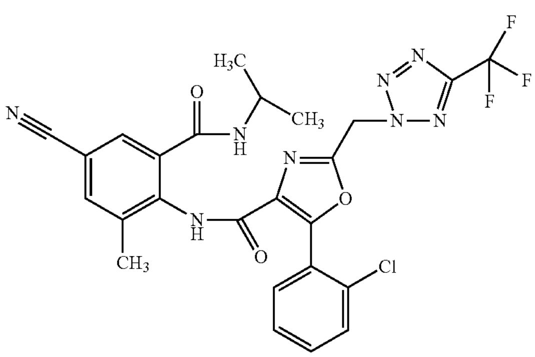 [SMILES: Cc1cc(C#N)cc(C(=O)NC(C)C)c1NC(=O)c1nc(Cn2nnc(C(F)(F)F)n2)oc1-c1ccccc1Cl] | 3.69 | 573 | (10.359;2.98),(10.099;0.48),(8.281;1.30),(8.262;1.35),(8.008;0.45),(7.885;0.45),(7.857;2.56),(7.784;2.64),(7.780;2.54),(7.765;0.46),(7.761;0.46),(7.657;1.41),(7.653;1.46),(7.638;1.76),(7.634;1.83),(7.613;1.15),(7.611;1.28),(7.593;2.56),(7.590;2.50),(7.574;1.37),(7.570;1.33),(7.556;1.79),(7.552;1.62),(7.535;0.94),(7.531;0.80),(7.504;0.44),(7.473;1.33),(7.469;1.29),(7.454;1.79),(7.451;1.74),(7.436;0.85),(7.432;0.73),(7.004;0.46),(6.624;8.55),(6.364;0.57),(3.958;0.71),(3.942;1.07),(3.923;1.10),(3.907;0.74),(3.376;0.35),(3.364;0.40),(3.347;0.48),(3.287;471.80),(3.248;0.38),(3.244;0.33),(2.878;1.70),(2.673;0.69),(2.668;0.87),(2.663;0.67),(2.576;0.51),(2.538;1.47),(2.508;50.27),(2.503;97.02),(2.499;128.26),(2.494;90.84),(2.490;42.88),(2.330;0.59),(2.326;0.80),(2.321;0.58),(2.286;1.87),(2.230;10.81),(2.214;1.02),(2.128;1.78),(2.067;0.60),(1.986;0.35),(1.237;0.36),(1.120;1.69),(1.103;1.70),(1.082;2.79),(1.074;0.72),(1.066;2.78),(1.050;2.44),(1.043;15.00),(1.034;2.95),(1.026;14.66),(−0.000;12.20),(−0.008;0.42) |
| 16 | 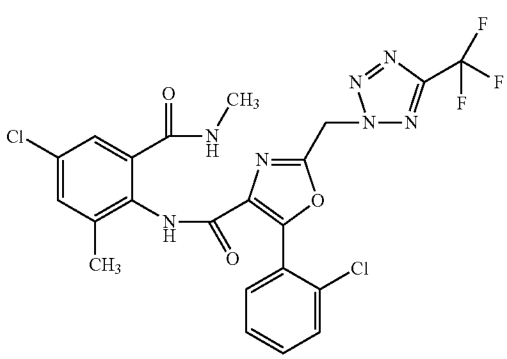 | 3.65 | 554 | (10.219;4.04),(10.143;0.33),(8.400;1.47),(8.389;1.48),(7.654;1.85),(7.650;2.01),(7.635;2.48),(7.631;2.54),(7.614;1.92),(7.611;1.97),(7.594;3.66),(7.591;3.64),(7.569;2.04),(7.565;2.04),(7.550;2.82),(7.546;2.63),(7.530;1.60),(7.526;1.33),(7.470;4.60),(7.464;3.64),(7.455;3.00),(7.451;2.67),(7.436;1.22),(7.433;1.16),(7.407;3.65),(7.401;3.05),(6.616;11.43),(6.573;0.65),(6.532;0.37),(6.352;0.69),(3.414;0.34),(3.389;0.44),(3.344;0.84),(3.341;0.83),(3.287;612.72),(2.726;0.40),(2.696;10.02),(2.685;10.00),(2.673;1.55),(2.668;1.39),(2.663;1.04),(2.620;0.78),(2.608;0.73),(2.572;0.72),(2.538;2.21),(2.521;5.51),(2.508;68.34),(2.503;130.43),(2.499;171.28),(2.494;120.33),(2.490;56.02),(2.330;0.81),(2.326;1.06),(2.321;0.75),(2.226;0.87),(2.215;0.49),(2.177;15.00),(2.164;1.47),(2.110;0.38),(2.067;0.72),(2.029;0.84),(1.986;0.30),(1.238;0.49),(−0.000;18.38),(−0.008;0.61) |

-continued

| No. | Structure | log P | MH+ | NMR |
|---|---|---|---|---|
| 17 | 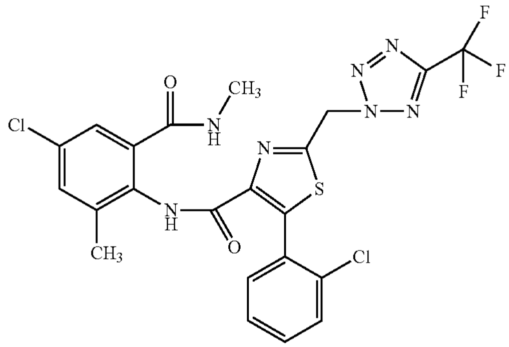 [SMILES: CNC(=O)c1cc(Cl)cc(C)c1NC(=O)c1nc(Cn2nnc(C(F)(F)F)n2)sc1-c1ccccc1Cl] | 3.73 | 589 | (10.154;3.08),(10.099;0.53),(8.293;1.21),(8.274;1.17),(8.003;0.40),(7.889;0.42),(7.824;2.25),(7.766;0.53),(7.761;0.59),(7.747;2.58),(7.743;2.34),(7.544;0.31),(7.518;1.29),(7.514;1.39),(7.498;2.27),(7.495;2.65),(7.489;1.20),(7.475;1.44),(7.470;1.60),(7.455;0.90),(7.450;1.04),(7.437;2.00),(7.432;1.51),(7.418;1.53),(7.410;1.69),(7.405;1.45),(7.391;1.44),(7.387;1.32),(7.372;0.47),(7.276;0.33),(7.003;0.45),(6.692;8.48),(6.633;0.54),(3.947;0.67),(3.930;1.00),(3.912;1.00),(3.895;0.69),(3.880;0.32),(3.359;0.47),(3.349;0.54),(3.340;0.68),(3.334;0.76),(3.288;465.72),(3.265;0.90),(3.250;0.42),(2.878;1.61),(2.677;0.37),(2.673;0.66),(2.668;0.84),(2.664;0.67),(2.538;1.40),(2.521;3.82),(2.508;48.03),(2.503;92.27),(2.499;121.60),(2.494;85.90),(2.490;40.32),(2.330;0.55),(2.326;0.77),(2.321;0.55),(2.286;1.81),(2.120;10.16),(2.067;0.57),(2.045;0.81),(1.399;0.57),(1.237;0.37),(1.220;0.59),(1.198;0.57),(1.181;0.58),(1.145;0.67),(1.120;1.71),(1.103;1.93),(1.085;14.93),(1.069;15.00),(1.057;1.61),(1.002;0.80),(0.986;0.80),(0.008;0.52),(−0.000;9.87),(−0.008;0.35) |
| 18 | 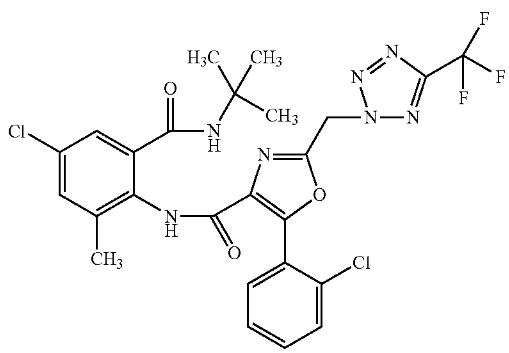 [SMILES: Cc1cc(Cl)cc(C(=O)NC(C)(C)C)c1NC(=O)c1nc(Cn2nnc(C(F)(F)F)n2)oc1-c1ccccc1Cl] | 4.46 | 596 | (9.792;1.00),(7.806;0.38),(7.680;0.95),(7.646;0.64),(7.643;0.52),(7.627;0.79),(7.624;0.68),(7.612;0.54),(7.609;0.53),(7.592;0.94),(7.589;0.94),(7.573;0.50),(7.569;0.50),(7.555;0.77),(7.535;0.54),(7.531;0.43),(7.477;0.54),(7.473;0.51),(7.458;0.65),(7.455;0.62),(7.439;0.41),(7.432;0.81),(7.427;0.84),(7.272;0.86),(7.267;0.81),(6.656;1.08),(6.618;2.85),(3.351;0.38),(3.339;0.53),(3.326;0.78),(3.287;405.26),(3.240;0.38),(2.673;0.57),(2.668;0.82),(2.664;0.56),(2.538;1.20),(2.521;3.46),(2.508;45.09),(2.503;86.46),(2.499;113.87),(2.494;80.41),(2.490;38.03),(2.335;0.34),(2.330;0.58),(2.326;0.79),(2.321;0.57),(2.221;0.35),(2.207;0.37),(2.183;3.52),(2.162;0.32),(2.084;1.27),(2.067;0.37),(1.976;0.31),(1.399;7.60),(1.323;0.87),(1.281;1.38),(1.258;0.82),(1.237;0.65),(1.182;1.48),(1.169;15.00),(0.008;0.63),(−0.000;12.07),(−0.008;0.46) |
| 19 | 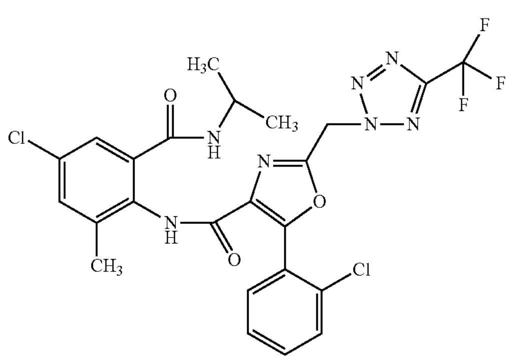 | 4.11 | 582 | (9.980;2.99),(8.130;1.34),(8.111;1.33),(7.644;1.40),(7.640;1.47),(7.625;1.77),(7.621;1.89),(7.606;1.25),(7.588;2.67),(7.585;2.67),(7.568;1.46),(7.564;1.58),(7.550;1.91),(7.546;1.94),(7.530;1.18),(7.525;0.97),(7.470;1.48),(7.466;1.50),(7.458;2.34),(7.451;3.95),(7.432;0.88),(7.429;0.87),(7.343;2.45),(7.337;2.39),(6.613;8.21),(6.569;0.48),(6.358;0.54),(3.936;0.65),(3.920;0.97),(3.902;0.99),(3.884;0.62),(3.359;0.33),(3.337;0.78),(3.286;821.35),(3.264;3.24),(3.243;1.02),(3.232;0.64),(3.217;0.47),(3.209;0.45),(3.181;0.33),(2.878;0.52),(2.672;1.20),(2.668;1.46),(2.663;1.13),(2.566;0.50),(2.538;2.18),(2.508;88.43),(2.503;172.72),(2.499;230.42),(2.494;164.79),(2.490;78.91),(2.421;0.34),(2.404;0.40),(2.334;0.69),(2.330;1.20),(2.326;1.60),(2.321;1.18),(2.218;0.73),(2.182;10.82),(2.165;1.05),(2.115;0.59),(2.067;0.80),(2.048;0.35),(2.002;0.64),(1.986;0.77),(1.237;0.58),(1.175;0.42),(1.143;1.24),(1.130;0.61),(1.119;0.60),(1.113;0.62),(1.103;0.52),(1.064;1.06),(1.047;0.99),(1.019;1.95),(1.010;15.00),(0.993;14.69),(0.008;1.51),(−0.000;31.10),(−0.008;1.13) |

-continued

| No. | Structure | log P | MH+ | NMR |
|---|---|---|---|---|
| 20 | (structure) | 3.45 | 540 | (10.319;3.92),(10.272;0.43),(7.945;1.77),(7.658;2.01),(7.654;2.21),(7.639;2.68),(7.635;2.80),(7.613;1.88),(7.610;2.08),(7.593;3.63),(7.590;3.72),(7.569;2.87),(7.565;3.49),(7.551;3.28),(7.547;2.87),(7.531;1.73),(7.527;1.50),(7.474;4.37),(7.468;4.27),(7.454;6.22),(7.448;2.86),(7.440;1.60),(7.436;1.46),(7.416;0.31),(6.600;11.06),(6.573;0.43),(6.524;0.63),(6.336;0.84),(4.058;0.44),(4.040;1.23),(4.022;1.24),(4.004;0.38),(3.376;0.35),(3.288;811.89),(3.263;2.05),(3.236;0.45),(3.226;0.38),(2.908;2.63),(2.673;1.00),(2.668;1.33),(2.664;1.00),(2.562;0.76),(2.538;2.22),(2.521;5.77),(2.508;78.08),(2.503;151.32),(2.499;200.22),(2.494;141.72),(2.490;66.55),(2.331;0.99),(2.326;1.33),(2.321;0.95),(2.220;0.57),(2.211;0.94),(2.174;15.00),(2.157;1.59),(2.109;0.87),(2.067;0.43),(2.049;0.34),(2.005;0.46),(1.986;5.36),(1.399;0.40),(1.260;0.34),(1.237;0.70),(1.193;1.55),(1.175;3.07),(1.157;1.52),(−0.000;8.81) |
| 21 | (structure) | 3.72 | 598 | (10.220;4.05),(10.145;0.36),(8.404;1.53),(8.393;1.42),(7.667;0.62),(7.653;1.92),(7.649;2.05),(7.634;2.56),(7.630;2.57),(7.614;2.16),(7.11;2.36),(7.595;6.70),(7.591;4.84),(7.569;2.02),(7.565;2.02),(7.550;2.78),(7.546;2.51),(7.530;4.78),(7.526;3.86),(7.473;1.99),(7.470;1.88),(7.455;2.69),(7.452;2.48),(7.436;1.17),(7.433;1.10),(6.614;11.44),(6.570;0.45),(6.532;0.52),(6.350;0.72),(5.742;1.36),(3.457;0.34),(3.444;0.40),(3.433;0.39),(3.422;0.51),(3.406;0.47),(3.372;0.78),(3.361;0.98),(3.350;1.26),(3.291;1150.47),(3.263;1.94),(3.245;0.46),(3.240;0.43),(2.694;10.26),(2.683;10.38),(2.668;1.93),(2.664;1.38),(2.618;0.63),(2.607;0.62),(2.588;0.41),(2.571;0.77),(2.538;2.70),(2.521;6.72),(2.508;88.67),(2.504;171.37),(2.499;226.67),(2.495;160.36),(2.490;75.44),(2.330;1.14),(2.326;1.38),(2.322;0.96),(2.222;0.58),(2.210;0.65),(2.173;15.00),(2.161;1.60),(2.105;0.80),(2.067;1.58),(2.049;0.34),(2.024;0.59),(1.399;0.33),(1.237;0.69),(1.143;0.50),(0.891;0.31),(−0.000;5.52) |
| 22 | (structure) | 4.52 | 640 | (9.788;0.98),(7.689;1.04),(7.672;0.31),(7.669;0.32),(7.646;0.59),(7.642;0.54),(7.627;0.81),(7.623;0.71),(7.609;0.56),(7.593;0.96),(7.589;0.99),(7.573;0.60),(7.569;0.78),(7.564;0.88),(7.560;0.94),(7.555;0.95),(7.551;0.77),(7.535;0.52),(7.477;0.48),(7.473;0.49),(7.458;0.68),(7.455;0.70),(7.439;0.30),(7.436;0.30),(7.393;0.85),(7.387;0.82),(6.655;0.69),(6.616;2.82),(3.290;390.54),(2.914;2.43),(2.673;0.47),(2.668;0.65),(2.664;0.52),(2.538;1.09),(2.521;2.74),(2.508;36.60),(2.504;70.94),(2.499;94.11),(2.494;66.79),(2.490;31.47),(2.330;0.49),(2.326;0.60),(2.321;0.46),(2.316;0.46),(2.217;0.31),(2.180;3.53),(2.159;0.31),(2.079;0.85),(2.067;0.60),(1.655;1.38),(1.399;9.88),(1.336;0.32),(1.323;1.12),(1.284;1.36),(1.258;7.15),(1.247;0.43),(1.237;0.50),(1.181;1.56),(1.169;15.00),(0.008;0.43),(−0.000;9.05),(−0.008;0.32) |
| 23 | (structure) | 4.21 | 626 | (9.984;2.89),(8.141;134),(8.122;1.34),(7.644;1.34),(7.640;1.49),(7.624;1.79),(7.621;1.87),(7.605;1.39),(7.588;4.43),(7.585;4.98),(7.568;1.48),(7.564;1.51),(7.550;1.92),(7.546;1.78),(7.530;1.04),(7.525;0.90),(7.466;3.66),(7.460;2.64),(7.451;2.14),(7.448;1.83),(7.432;0.97),(7.429;0.92),(6.613;8.29),(6.567;0.48),(6.514;0.39),(6.357;0.52),(3.952;0.31),(3.935;0.67),(3.919;1.05),(3.902;0.97),(3.884;0.64),(3.355;0.35),(3.286;656.24),(3.240;0.57),(3.230;0.45),(3.223;0.42),(3.216;0.38),(3.210;0.37),(2.877;1.93),(2.677;0.58),(2.672;1.04),(2.668;1.29),(2.663;0.92),(2.566;0.40),(2.538;2.12),(2.521;5.52),(2.508;76.68),(2.503;148.33),(2.499;196.43),(2.494;139.48),(2.490;66.19),(2.421;0.35),(2.335;0.66),(2.330;1.00),(2.326;1.31),(2.321;0.91),(2.215;0.71),(2.179;10.77),(2.162;1.07),(2.115;0.67),(2.067;1.64),(2.049;0.40),(1.997;0.58),(1.440;0.31),(1.423;0.30),(1.399;2.60),(1.238;0.54),(1.143;1.66),(1.130;0.79),(1.119;1.96),(1.114;0.96),(1.103;1.87),(1.067;1.04),(1.050;0.94),(1.020;2.05),(1.011;15.00),(0.994;14.70),(0.008;1.51),(−0.000;30.14),(−0.009;1.12) |

-continued

| No. | Structure | log P | MH+ | NMR |
|---|---|---|---|---|
| 24 | 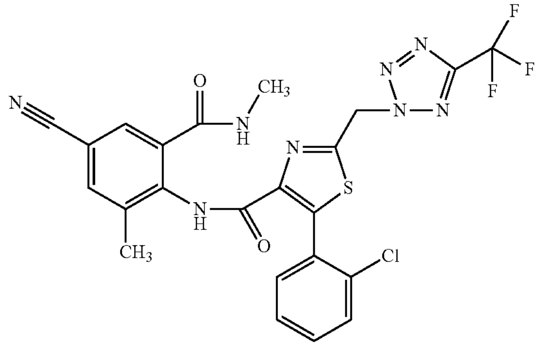 | 3.46 | 560 | (10.654;3.64),(10.169;0.62),(8.497;1.42),(8.485;1.47),(8.410;0.31),(8.398;0.33),(7.996;0.58),(7.992;0.56),(7.893;0.56),(7.826;3.47),(7.796;4.36),(7.570;2.00),(7.567;2.07),(7.550;3.17),(7.547;3.10),(7.539;1.98),(7.535;2.12),(7.520;2.60),(7.516;2.82),(7.486;1.35),(7.482;1.43),(7.467;2.60),(7.463;2.12),(7.448;1.70),(7.443;1.40),(7.425;0.41),(7.413;1.96),(7.410;1.96),(7.394;2.57),(7.391;2.46),(7.376;1.02),(7373;0.91),(6.960;0.61),(6.718;12.51),(6.477;0.51),(4.058;0.38),(4.040;1.03),(4.022;1.11),(4.004;0.39),(3.440;0.35),(3.426;0.30),(3.400;0.37),(3.375;0.63),(3.346;0.97),(3.328;1.75),(3.289;892.22),(3.254;0.94),(2.857;3.05),(2.742;1.05),(2.731;1.07),(2.697;2.06),(2.680;10.17),(2.668;11.07),(2.650;0.58),(2.582;1.83),(2.569;1.85),(2.538;2.40),(2.521;6.13),(2.508;82.52),(2.504;159.84),(2.499;211.72),(2.494;149.90),(2.490;70.75),(2.330;0.97),(2326;127),(2.321;0.98),(2.277;2.42),(2.244;0.32),(2.159;15.00),(2.141;1.14),(2.132;2.52),(2.098;1.40),(2.067;0.38),(2.049;0.35),(1.986;4.67),(1.238;0.45),(1.193;1.32),(1.175;2.65),(1.157;1.28),(-0.000;7.74) |
| 25 | 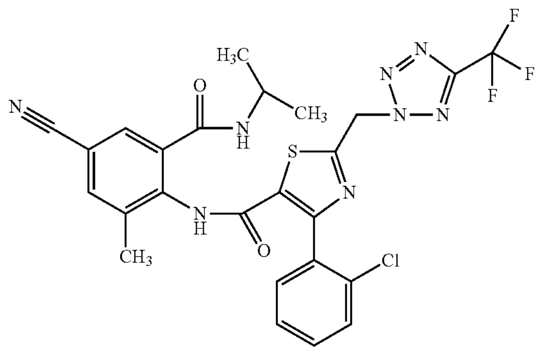 | 3.7 | 589 | (10.154;3.08),(10.099;0.53),(8.293;1.21),(8.274;1.17),(8.003;0.40),(7.889;0.42),(7.824;2.25),(7.766;0.53),(7.761;0.59),(7.747;2.58),(7.743;2.34),(7.544;0.31),(7.518;1.29),(7.514;1.39),(7.498;2.27),(7.495;2.65),(7.489;1.20),(7.475;1.44),(7.470;1.60),(7.455;0.90),(7.450;1.04),(7.437;2.00),(7.432;1.51),(7.418;1.53),(7.410;1.69),(7.405;1.45),(7.391;1.44),(7.387;1.32),(7.372;0.47),(7.276;0.33),(7.003;0.45),(6.692;8.48),(6.633;0.54),(3.947;0.67),(3.930;1.00),(3.912;1.00),(3.895;0.69),(3.880;0.32),(3.359;0.47),(3.349;0.54),(3.340;0.68),(3.334;0.76),(3.288;465.72),(3.265;0.90),(3.250;0.42),(2.878;1.61),(2.677;0.37),(2.673;0.66),(2.668;0.84),(2.664;0.67),(2.538;1.40),(2.521;3.82),(2.508;48.03),(2.503;92.27),(2.499;121.60),(2.494;85.90),(2.490;40.32),(2.330;0.55),(2.326;0.77),(2.321;0.55),(2.286;1.81),(2.120;10.16),(2.067;0.57),(2.045;0.81),(1.399;0.57),(1.237;0.37),(1.220;0.59),(1.198;0.57),(1.181;0.58),(1.145;0.67),(1.120;1.71),(1.103;1.93),(1.085;14.93),(1.069;15.00),(1.057;1.61),(1.002;0.80),(0.986;0.80),(0.008;0.52),(-0.000;9.87),(-0.008;0.35) |
| 26 | 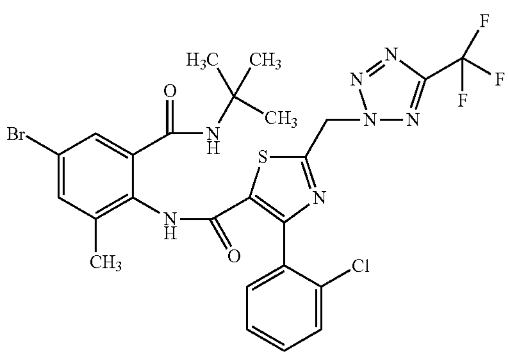 [SMILES: Cc1cc(Cl)cc(C(=O)NC(C)(C)C)c1NC(=O)c1sc(Cn2nnc(C(F)(F)F)n2)nc1-c1ccccc1Cl] | 4.69 | 656 | (9.644;0.89),(7.750;0.80),(7.531;1.06),(7.527;1.04),(7.511;0.69),(7.508;0.67),(7.488;0.33),(7.483;0.38),(7.470;0.53),(7.465;0.78),(7.447;0.66),(7.442;0.44),(7.428;0.45),(7.423;0.33),(7.415;0.50),(7.411;0.51),(7.392;1.21),(7.386;0.80),(6.690;2.52),(3.323;0.30),(3.285;179.92),(2.668;0.39),(2.538;0.61),(2.521;1.67),(2.508;22.60),(2.503;43.85),(2.499;58.18),(2.494;41.34),(2.490;19.66),(2.326;0.37),(2.048;3.46),(1.399;3.25),(1.257;15.00),(1.147;0.46),(-0.000;4.74) |
| 27 | 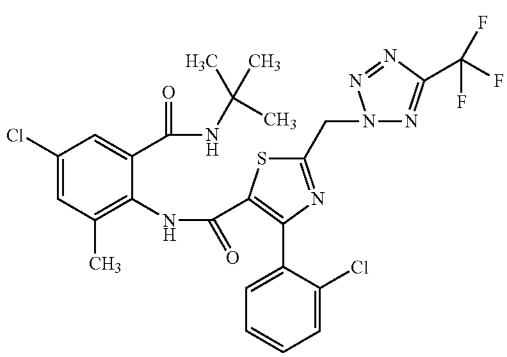 | 4.59 | 612 | (9.643;0.80),(7.736;0.80),(7.528;0.47),(7.509;0.72),(7.485;0.40),(7.465;0.81),(7.448;0.60),(7.428;0.40),(7.412;0.55),(7.396; 1.19),(7.272;0.79),(6.690;2.34),(3.370;0.42),(3.292;755.22),(2.673;0.72),(2.668;0.98),(2.664;0.71),(2.538;1.56),(2.521;3.96),(2.508;56.59),(2.504;109.81),(2.499;145.54),(2.494;103.80),(2.490;49.44),(2.330;0.70),(2.326;0.94),(2.321;0.68),(2.067;1.65),(2.051;4.07),(1.256;15.00),(1.237;0.91),(-0.000;3.07) |

| No. | Structure | log P | MH+ | NMR |
|---|---|---|---|---|
| 28 | 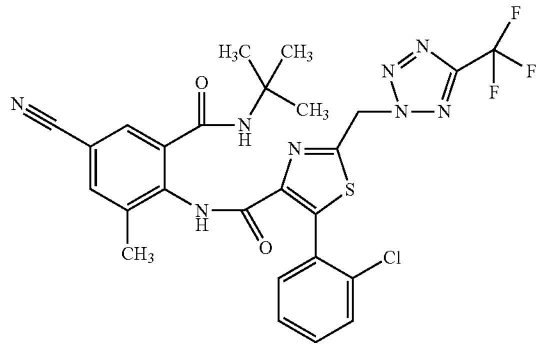 [SMILES: Cc1cc(C#N)cc(C(=O)NC(C)(C)C)c1NC(=O)c1nc(Cn2nnc(C(F)(F)F)n2)sc1-c1ccccc1Cl] | 4.29 | 603 | (10.188;1.04),(7.891;0.95),(7.795;0.79),(7.792;0.84), (7.698;0.90),(7.694;0.83),(7.558;0.45),(7.555;0.48), (7.538;0.75),(7.535;0.75),(7.520;0.45),(7.516;0.50), (7.501;0.61),(7.497;0.70),(7.483;0.35),(7.479;0.35), (7.465;0.64),(7.460;0.49),(7.445;0.41),(7.440;0.31), (7.411;0.48),(7.408;0.48),(7.393;0.64),(7.390;0.60), (6.689;3.03),(3.288;303.81),(2.914;3.10),(2.672;0.41), (2.668;0.54),(2.663;0.40),(2.538;0.93),(2.521;2.32), (2.508;30.06),(2.503;57.99),(2.499;76.67), (2.494;54.35),(2.490;25.58),(2.330;0.36), (2.326;0.48),(2.321;0.33), (2.166;3.66),(2.067;0.34),(1.399;2.40),(1.258;9.18), (1.169;15.00),(1.107;0.45),(−0.000;4.49) |
| 29 | 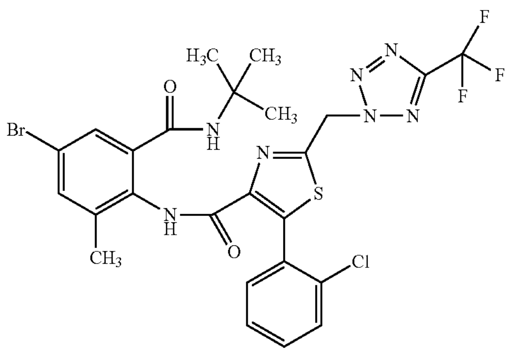 | 4.83 | 656 | (9.855;0.97),(7.735;0.93),(7.553;0.46),(7.550;0.48), (7.530;1.35),(7.523;0.82),(7.503;0.43),(7.498;0.46), (7.484;0.60),(7.480;0.75),(7.472;0.36),(7.458;0.66), (7.453;0.46),(7.438;0.41),(7.406;0.50),(7.403;0.46), (7.388;0.64),(7.384;0.60),(7.369;1.03),(7.365;0.88), (6.674;2.91),(3.289;260.58),(3.266;1.22),(2.890;0.32), (2.668;0.42),(2.538;0.70),(2.521;1.86),(2.508;23.16), (2.503;44.03),(2.499;57.70),(2.494;40.55), (2.490;18.90),(2.326;0.35),(2.118;3.61), (2.067;0.45),(1.137;15.00),(−0.000;1.72) |
| 30 | 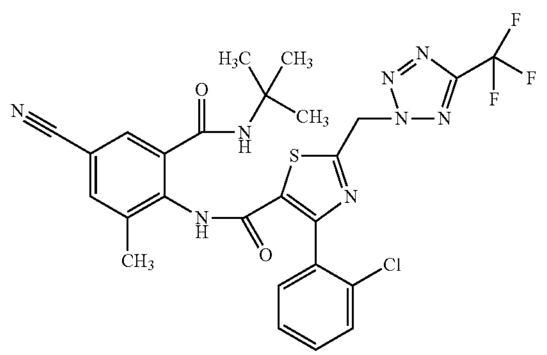 [SMILES: Cc1cc(C#N)cc(C(=O)NC(C)(C)C)c1NC(=O)c1sc(Cn2nnc(C(F)(F)F)n2)nc1-c1ccccc1Cl] | 4.07 | 603 | (9.995;1.09),(7.892;0.90),(7.798;0.76),(7.795;0.79), (7.712;0.87),(7.708;0.81),(7.530;0.41),(7.527;0.44), (7.510;0.65),(7.507;0.69),(7.496;0.40),(7.492;0.40), (7.478;0.58),(7.473;0.67),(7.461;0.31),(7.447;0.64), (7.442;0.46),(7.428;0.44),(7.422;0.36),(7.418;0.53), (7.414;0.51),(7.399;0.53),(7.396;0.48),(6.697;3.01), (3.289;191.50),(2.668;0.35),(2.538;0.60),(2.521;1.48), (2.508;19.64),(2.503;37.90),(2.499;50.12), (2.494;35.46),(2.490;16.65),(2.326;0.31), (2.095;3.50),(2.084;0.88), (1.274;15.00),(1.107;0.34),(0.008;0.31),(−0.000;6.22) |
| 31 | 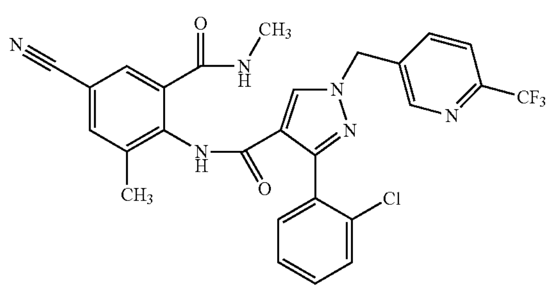 [SMILES: CNC(=O)c1cc(C#N)cc(C)c1NC(=O)c1cn(Cc2ccc(C(F)(F)F)nc2)nc1-c1ccccc1Cl] | 2.78 2.83 | 553 | (9.907;3.99),(9.902;4.46),(8.798;2.03),(8.594;5.64), (8.434;1.02),(8.423;1.09),(8.372;3.44),(8.251;7.12), (8.064;0.99),(8.040;1.43),(7.981;2.58),(7.960;1.65), (7.845;2.19),(7.824;4.36),(7.818;2.90),(7.808;2.98), (7.756;2.74),(7.752;2.64),(7.741;3.23),(7.737;2.81), (7.697;1.53),(7.680;1.20),(7.544;1.00),(7.528;2.76), (7.517;1.38),(7.511;1.32),(7.502;1.64),(7.496;1.94), (7.481;0.88),(7.476;1.43),(7.469;1.17),(7.460;1.76), (7.455;4.07),(7.448;4.23),(7.437;2.52),(7.429;2.65), (7.425;1.53),(7.412;1.93),(7.406;2.19),(7.397;0.90), (7.384;2.02),(7.379;1.35),(7.366;3.02),(7.361;2.20), (7.348;1.49),(7.344;1.13),(5.661;5.52),(5.360;0.85), (5.321;2.82),(5.291;2.72),(5.252;0.89),(3.394;0.79), (3.331;2.89),(3.289;1820.16),(3.241;1.54),(3.077;1.03), (2.678;8.35),(2.668;15.00),(2.657;9.02),(2.610;0.60), (2.576;0.87),(2.538;4.94),(2.521;12.93),(2.508;167.56), (2.503;322.86),(2.499;426.89),(2.494;301.29), (2.490;141.85),(2.330;2.07),(2.326;2.69), (2321;1.95),(2.201;10.77), (2.175;12.79),(2.067;1.01),(2.049;0.60),(1.237;1.07), (1.107;3.59),(0.008;2.21),(−0.000;42.38),(−0.008;1.53) |

-continued

| No. | Structure | log P | MH+ | NMR |
|---|---|---|---|---|
| 32 | 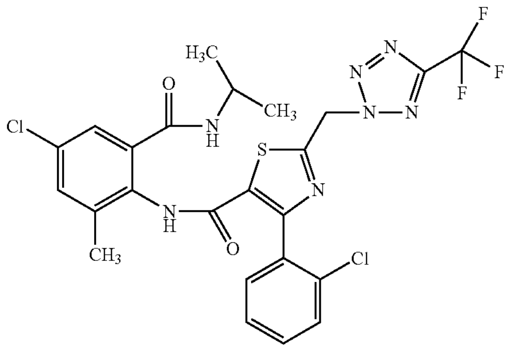 [SMILES: Cc1cc(Cl)cc(C(=O)NC(C)C)c1NC(=O)c1sc(Cn2nnc(C(F)(F)F)n2)nc1-c1ccccc1Cl] | 4.15 | 598 | (9.805;2.15),(8.191;0.89),(8.172;0.92),(7.521;0.98),(7.517;1.20),(7.501;1.72),(7.498;1.88),(7.490;0.78),(7.486;0.81),(7.468;1.16),(7.457;0.80),(7.452;0.89),(7.438;1.94),(7.433;2.46),(7.426;1.73),(7.419;1.48),(7.413;1.12),(7.409;1.15),(7.405;1.14),(7.391;1.07),(7.387;1.02),(7.369;0.39),(7.320;2.29),(7.314;2.09),(6.688;6.51),(3.942;0.55),(3.925;0.83),(3.907;0.83),(3.890;0.55),(3.307;1395.40),(3.286;2.93),(3.284;2.99),(3.261;0.57),(3.251;0.48),(2.678;0.40),(2.674;0.92),(2.669;1.32),(2.664;0.97),(2.660;0.39),(2.539;1.82),(2.523;2.96),(2.518;4.47),(2.509;69.12),(2.505;138.11),(2.500;189.23),(2.496;128.68),(2.491;60.03),(2.336;0.43),(2.331;0.97),(2.327;1.33),(2.322;0.94),(2.318;0.45),(2.076;8.52),(2.049;0.37),(1.236;0.48),(1.068;15.00),(1.051;14.92),(−0.000;5.23) |
| 33 | 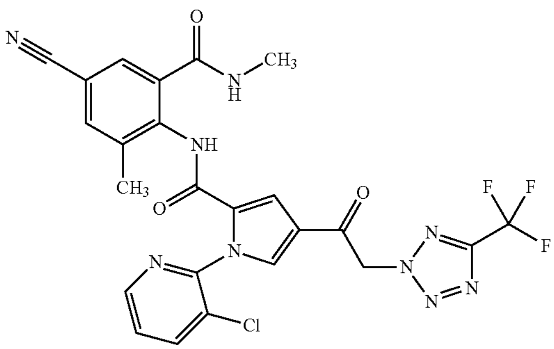 [SMILES: CNC(=O)c1cc(C#N)cc(C)c1NC(=O)c1cc(C(=O)Cn2nnc(C(F)(F)F)n2)cn1-c1ncccc1Cl] | 2.75 | 572 | (10.327;4.85),(8.523;3.11),(8.519;3.40),(8.511;3.41),(8.508;3.34),(8.373;4.68),(8.369;4.70),(8.358;0.92),(8.346;1.84),(8.335;1.85),(8.160;2.69),(8.156;2.75),(8.139;2.90),(8.136;2.84),(7.839;3.72),(7.749;4.03),(7.745;3.90),(7.699;4.39),(7.695;4.43),(7.608;2.71),(7.596;2.64),(7.588;2.60),(7.576;2.74),(6.615;13.56),(4.095;0.52),(4.039;0.54),(4.021;0.61),(3.341;2.34),(3.304;2412.98),(3.281;8.17),(3.263;1.33),(3.241;0.61),(3.232;0.67),(2.858;7.44),(2.716;1.07),(2.704;1.18),(2.684;11.00),(2.673;12.46),(2.664;3.07),(2.660;1.45),(2.581;3.88),(2.568;3.91),(2.539;5.04),(2.522;8.01),(2.518;11.83),(2.509;157.46),(2.504;311.75),(2.500;425.12),(2.495;294.21),(2.491;140.21),(2.336;1.02),(2.331;2.05),(2.327;2.89),(2.322;2.02),(2.273;1.38),(2.209;16.00),(2.069;2.95),(2.049;0.66),(1.987;2.63),(1.258;0.50),(1.237;2.61),(1.193;0.97),(1.175;1.70),(1.157;1.00),(1.127;0.73),(1.113;1.96),(1.109;1.50),(1.098;1.95),(1.091;0.79),(0.008;2.33),(−0.000;72.01),(−0.008;2.37) |
| 34 | 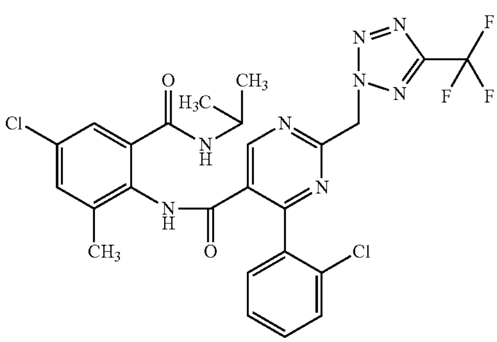 [SMILES: Cc1cc(Cl)cc(C(=O)NC(C)C)c1NC(=O)c1cnc(Cn2nnc(C(F)(F)F)n2)nc1-c1ccccc1Cl] | 3.91 | 593 | (10.259;0.31),(10.240;3.40),(9.133;6.05),(8.266;1.50),(8.246;1.50),(7.517;1.05),(7.500;2.72),(7.489;1.52),(7.483;1.51),(7.473;1.54),(7.467;2.01),(7.461;1.17),(7.455;1.62),(7.448;1.85),(7.441;3.23),(7.432;2.84),(7.427;3.73),(7.420;3.53),(7.397;0.59),(7.393;0.54),(7.325;2.90),(7.319;2.75),(6.605;8.47),(6.398;0.58),(3.973;0.65),(3.956;1.00),(3.939;1.00),(3.921;0.65),(3.306;374.18),(3.210;0.42),(2.674;0.48),(2.669;0.61),(2.664;0.48),(2.539;1.46),(2.504;69.08),(2.500;86.17),(2.496;62.29),(2.425;0.39),(2.327;0.69),(2.322;0.54),(2.069;0.93),(2.031;11.83),(2.012;0.73),(1.987;0.32),(1.398;1.91),(1.237;0.35),(1.087;14.95),(1.071;15.00),(1.035;0.45),(1.018;0.38),(−0.000;6.72) |
| 35 | 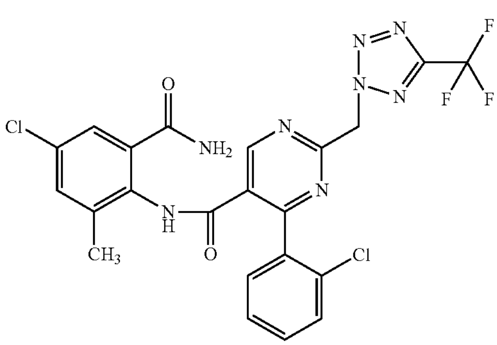 [SMILES: Cc1cc(Cl)cc(C(N)=O)c1NC(=O)c1cnc(Cn2nnc(C(F)(F)F)n2)nc1-c1ccccc1Cl] | 3.01 | 551 | (10.344;0.30),(10.334;0.33),(10.305;4.35),(9.179;0.35),(9.142;7.79),(7.840;2.15),(7.526;1.57),(7.513;1.55),(7.507;2.75),(7.502;2.79),(7.489;1.75),(7.483;2.35),(7.474;3.04),(7.467;4.83),(7.462;6.42),(7.457;5.47),(7.451;5.07),(7.445;4.32),(7.439;4.51),(7.434;5.23),(7.414;0.86),(7.393;4.11),(7.387;3.31),(6.603;10.93),(6.394;0.53),(3.530;0.31),(3.471;0.50),(3.308;991.99),(3.238;1.02),(3.192;0.41),(3.128;0.30),(2.731;0.31),(2.694;0.30),(2.673;1.07),(2.669;1.34),(2.609;0.47),(2.592;0.55),(2.539;8.38),(2.508;80.27),(2.504;141.87),(2.500;179.30),(2.496;126.41),(2.412;0.35),(2.331;0.96),(2.326;1.23),(2.322;0.94),(2.097;0.40),(2.084;3.55),(2.069;3.08),(2.058;15.00),(1.987;0.50),(1.907;0.30),(1.398;10.46),(1.292;0.35),(1.235;0.65),(1.107;0.30),(0.890;0.43),(−0.000;2.02) |

-continued
| No. | Structure | log P | MH+ | NMR |
|---|---|---|---|---|
| 36 | 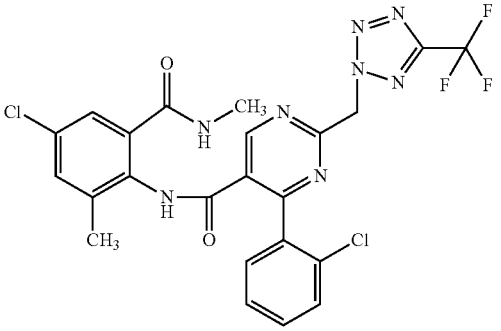 [SMILES: CNC(=O)c1cc(Cl)cc(C)c1NC(=O)c1cnc(Cn2nnc(C(F)(F)F)n2)nc1-c1ccccc1Cl] | 3.31 | 565 | (10.313;0.31),(10.306;0.34),( 10.279;4.50),(9.170;0.54), (9.134;7.99),(8.332;1.74),(8321;1.67),(7.522;1.48), (7.504;3.64),(7.489;1.82),(7.483;2.00),(7.473;2.16), (7.467;2.72),(7.461;1.62),(7.454;2.16),(7.448;2.71), (7.441;5.03),(7.436;5.73),(7.431;6.60),(7.414;2.28), (7.411;2.17),(7.395;0.83),(7.391;0.70),(7.350;4.07), (7.344;3.61),(6.604;11.12),(6.394;0.59),(4.039;0.38), (4.021;0.37),(3.303;442.85),(2.691;9.96),(2.680;9.72), (2.669;1.46),(2.664;1.01),(2.539;2.09),(2.508;49.81), (2.504;87.03),(2.500;108.65),(2.495;75.66),(2.335;0.40), (2.331;0.64),(2.326;0.82),(2.322;0.62),(2.069;0.80), (2.040;15.00),(1.987;1.62),(1.398;2.22),(1.237;0.68), (1.224;030),(1.192;0.52),(1.175;0.89),(1.157;0.47), (0,890;0.34),(−0.000;7.17),(−0.008;0.37) |
| 37 | 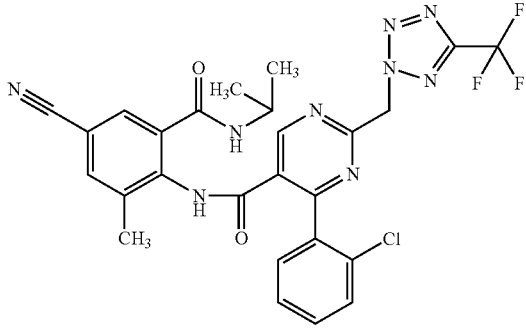 [SMILES: Cc1cc(C#N)cc(C(=O)NC(C)C)c1NC(=O)c1cnc(Cn2nnc(C(F)(F)F)n2)nc1-c1ccccc1Cl] | 3.5 | 584 | (10.506;2.95),(9.149;4.91),(8.326;1.31),(8.307;1.29), (7.826;2.56),(7.762;0.34),(7.739;2.88),(7.735;2.72), (7.517;0.93),(7.498;2.65),(7.490;1.56),(7.483;1.42), (7.474;1.46),(7.468;2.16),(7.457;1.24),(7.448;2.44), (7.444;2.81),(7.438;2,84),(7.434;2.11),(7.422;1.28), (7.418;1.24),(7.403;0.46),(7.399;0.40),(6.616;7.82), (6.407;0.33),(4.039;0.38),(4.021;0.40),(3.960;0.61), (3.943;0.97),(3.925;0.95),(3.909;0.61),(3.301;252.17), (2.673;0.51),(2.669;0.67),(2.664;0.51),(2.539;1.64), (2.508;40.24),(2.504;70.87),(2.500;89.15),(2.495;62.26), (2.331;0.53),(2.326;0.68),(2.322;0.50).(2.286;1.24), (2.126;1.28),(2.089;9.46),(2.069;0.71),(1.987;1.72), (1.398;8.09),(1.237;0.70),(1.193;0.55),(1.175;1.01), (1.157;0.57),(1.088;15.00),(1.081;4.76),(1.072;14.94), (1.065;3.62),(−0.000;5.45) |
| 38 | 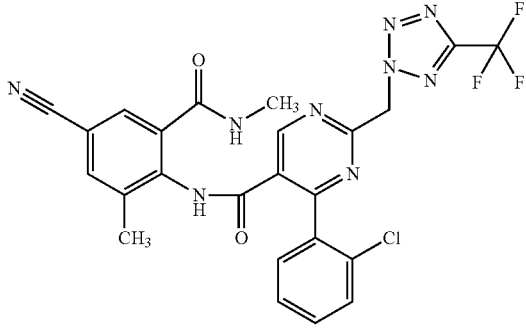 [SMILES: CNC(=O)c1cc(C#N)cc(C)c1NC(=O)c1cnc(Cn2nnc(C(F)(F)F)n2)nc1-c1ccccc1Cl] | 2.93 | 556 | (10.544;4.62),(10.173;0.58),(9.188;0.31),(9.149;7.22), (8.418;2.11),(8.407;1.91),(7.997;0.57),(7.900;0.62), (7.837;4.14),(7.802;0.63),(7.756;4.51),(7.522;1.71), (7.518;1.63),(7.504;4.47),(7.491;2.20),(7.485;2.14), (7.475;2.63),(7.469;3.94),(7.464;2.44),(7.451;5.83), (7.438;2.94),(7.435;2.67),(7.423;2.36),(7.403;0.59), (6.965;0.58),(6.614;11.96),(6.403;0.50),(4.039;0.96), (4.021;0.97),(4.004;0.36),(3.536;0.30),(3.517;0.36), (3.502;0.41),(3.483;0.43),(3.311;938.39),(3.288;14.63), (3.230;0.62),(3.206;0.35),(2.693;10.41),(2.682;10.28), (2.670;1.90),(2.639;0.33),(2.539;3.24),(2.505;117.82), (2.500;147.75),(2.496;104.00),(2.403;0.34),(2.327;1.07), (2.323;0.77),(2.277;2.49),(2.131;2.72),(2.099;15.00), (2.069;1.63),(2.050;0.44),(1.987;3.86),(1.908;0.78), (1.237;0.55),(1.193;1.05),(1.175;2.08),(1.157;1.11), (0.890;0.32),(−0.000;5.25) |
| 39 | 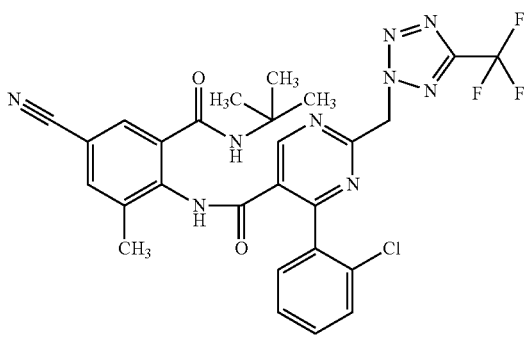 [SMILES: Cc1cc(C#N)cc(C(=O)NC(C)(C)C)c1NC(=O)c1cnc(Cn2nnc(C(F)(F)F)n2)nc1-c1ccccc1Cl] | 3.85 | 598 | (10.470;1.10),(9.121;1.91),(7.999;0.93),(7.795;0.93), (7.717;0.99),(7.713;0.94),(7.525;0.38),(7.506;0.96), (7.492;0.38),(7.484;0.41),(7.479;0.41),(7.470;0.61), (7.451;0.65),(7.438;1.64),(7.424;0.51),(6.618;2.84), (3.302;127.15),(3.278;2.95),(2.539;0.66),(2.504;28.83), (2.500;35.92),(2.496;25.60),(2.065;3.49),(1.288;15.00), (1.276;1.38),(1.263;0.93),(−0.000;2.18) |

-continued

| No. | Structure | log P | MH+ | NMR |
|---|---|---|---|---|
| 40 | (structure) | 2.69 | 542 | (10.590;2.35),(9.193;0.39),(9.183;0.38),(9.156;15.00),(8.041;1.12),(8.005;0.41),(7.988;0.50),(7.926;1.50),(7.898;1.33),(7.878;0.85),(7.853;1.74),(7.806;6.03),(7.609;0.36),(7.590;0.48),(7.567;1.01),(7.550;1.09),(7.519;4.86),(7.499;6.00),(7.461;7.24),(7.446;7.00),(7.425;2.84),(7.024;0.61),(6.605;12.82),(6.396;0.63),(4.057;1.11),(4.039;3.02),(4.021;3.03),(4.004;1.09),(3.457;0.49),(3.430;0.64),(3.424;0.74),(3.305;1129.01),(3.181;0.50),(3.145;0.42),(2.891;0.38),(2.731;0.39),(2.695;0.40),(2.674;1.34),(2.669;1.74),(2.664;1.32),(2.622;0.41),(2.615;0.47),(2.594;0.63),(2.579;0.81),(2.539;11.18),(2.508;110.51),(2.504;193.28),(2.500;241.77),(2.496;168.56),(2.402;0.64),(2.394;0.53),(2.384;0.45),(2.331;1.47),(2.326;1.86),(2.267;2.76),(2.245;0.48),(2.214;0.38),(2.199;0.38),(2.188;0.41),(2.175;0.51),(2.170;0.50),(2.130;5.98),(2.109;13.59),(2.069;2.56),(2.050;1.25),(2.039;0.62),(2.004;0.47),(1.987;13.11),(1.955;0.45),(1.905;1.06),(1.398;0.98),(1.299;0.38),(1.293;0.52),(1.260;0.42),(1.238;1.01),(1.193;3.67),(1.175;7.14),(1.157;3.56),(0.890;0.63),(−0.000;5.60) |
| 41 | (structure) | 4.33 | 607 | (10.253;0.36),(9.108;0.47),(7.980;0.34),(7.513;0.34),(7.433;0.67),(7.401;0.53),(7.286;0.41),(6.623;0.73),(3.380;1.74),(3.352;3952.17),(3.328;126.58),(2.621;1.58),(2.618;3.42),(2.615;4.70),(2.612;3.36),(2.609;1.54),(2.524;9.15),(2.521;11.75),(2.518;11.99),(2.509;248.89),(2.506;532.96),(2.503;720.27),(2.500;512.66),(2.497;229.26),(2.393;1.41),(2.390;3.23),(2.387;4.47),(2.384;3.12),(2.381;1.32),(2.205;0.31),(2.076;13.50),(2.008;1.15),(1.286;3.52),(1.234;0.82),(0.005;1.05),(0.000;31.06),(−0.006;0.87) |
| 42 | (structure) | 3.31 | 543 | (10.13;3.41),(8.42;0.54),(8.41;1.46),(8.40;1.46),(8.40;0.53),(7.82;2.98),(7.82;3.16),(7.73;3.52),(7.73;3.35),(7.54;2.25),(7.53;1.70),(7.53;1.52),(7.52;1.91),(7.52;2.77),(7.44;1.51),(7.44;1.21),(7.44;1.37),(7.43;1.57),(7.43;1.69),(7.43;3.79),(7.42;1.28),(7.41;3.46),(7.41;4.82),(7.40;6.03),(7.40;3.59),(7.39;1.96),(7.38;0.54),(7.35;3.51),(7.35;3.70),(7.24;3.77),(7.23;3.71),(6.05;10.18),(3.57;0.47),(3.36;612.67),(3.34;4.50),(2.66;11.78),(2.65;11.98),(2.62;0.52),(2.62;0.74),(2.61;0.53),(2.54;0.40),(2.52;1.46),(2.52;1.83),(2.52;1.76),(2.51;38.01),(2.51;83.37),2.50;114.48),(2.50;81.76),(2.50;37.64),(2.39;0.50),(2.39;0.75),(2.38;0.51),(2.17;16.00),(2.08;0.81),(1.99;0.60),(1.17;0.33) |
| 43 | (structure) | 3.75 | 552 | (9.78;4.26),(8.21;1.64),(8.20;1.57),(7.53;1.70),(7.52;1.98),(7.52;1.38),(7.51;1.96),(7.51;1.85),(7.51;1.83),(7.50;0.54),(7.43;1.03),(7.42;3.24),(7.41;10.53),(7.40;7.79),(7.39;6.50),(7.38;1.64),(7.37;0.37),(7.31;7.67),(7.31;6.69),(7.19;3.97),(7.18;3.66),(6.04;9.99),(3.49;0.32),(3.48;0.33),(3.46;0.39),(3.44;0.50),(3.31;872.39),(3.29;10.05),(2.83;0.57),(2.74;0.62),(2.67;1.44),(2.65;10.20),(2.64;10.15),(2.58;0.86),(2.54;1.82),(2.51;59.15).(2.50;105.95),(2.50;135.20),(2.50;95.17),(2.49;47.00),(2.43;0.35),(2.33;0.73),(2.33;0.96),(2.32;0.71),(2.16;0.39),(2.13;16.00),(2.11;0.83),(2.07;0.50),(0.00;7.85) |

| No. | Structure | log P | MH+ | NMR |
|---|---|---|---|---|
| 44 | [structure: chlorobenzamide with N-methyl, linked to methyl-substituted aniline, pyrrole with 2-chlorophenyl, and tetrazole-CH2 bearing pentafluoroethyl] | 4.09 | 602 | (9.81;4.38),(8.23;1.61),(8.22;1.58),(7.53;1.61),(7.53;1.61),(7.52;1.19),(7.52;1.84),(7.51;1.97),(7.50;0.33),(7.44;0.85),(7.42;1.87),(7.42;1.98),(7.41;7.52),(7.41;7.57),(7.41;7.38),(7.41;6.82),(7.40;5.39),(7.39;1.10),(7.38;1.74),(7.32;4.26),(7.32;4.55),(7.31;3.99),(7.31;3.34),(7.19;3.85),(7.18;3.59),(6.07;9.67),(3.32;335.26),(3.30;3.75),(3.08;1.03),(2.67;0.76),(2.67;0.60),(2.65;10.04),(2.64;10.11),(2.54;0.34),(2.52;1.23),(2.51;86.86),(2.50;113.84),(2.50;78.39),(2.33;0.69),(2.13;16.00),(2.07;0.87),(1.24;0.34),(1.11;2.98),(0.00;6.08) |

Analytical Methods:

The logP values reported in the table above and in the Preparation Examples were determined in accordance with EEC Directive 79/831 Annex V.A8 by HPLC (High Performance Liquid Chromatography) on reversed-phase columns (C 18), with the following methods:

The LC-MS determination in the acidic range is carried out at pH 2.7 using the mobile phases 0.1% aqueous formic acid and acetonitrile (contains 0.1% formic acid), linear gradient from 10% acetonitrile to 95% acetonitrile Calibration was carried out using unbranched alkan-2-ones (having from 3 to 16 carbon atoms) with known logP values (the logP values were determined by the retention times using linear interpolation between two successive alkanones).

The lambda max values were determined in the maxima of the chromatographic signals using the UV spectra from 200 nm to 400 nm.

The MH+ signals were determined using an Agilent MSD system with ESI and positive or negative ionisation.

The NMR spectra were determined using a Bruker Avance 400 fitted with a flow probe head (volume 60 μl). The solvent used was d6-DMSO, with tetramethylsilane (0.00 ppm) being employed as reference. The examples in the table above were recorded in d6-DMSO as solvent. The measuring temperature was 303K.

In individual cases, the samples were measured using a Bruker Avance II 600 or III 600.

USE EXAMPLES

Example 1

*Spodoptera frugiperda* Test

SPODFR Spray Treatment

Solvents: 78.0 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amount of solvents and emulsifier, and the concentrate is diluted with emulsifier-containing water to the desired concentration. Discs of maize leaves (*Zea mays*) are sprayed with an active compound preparation of the desired concentration and, after drying, populated with caterpillars of the armyworm (*Spodoptera frugiperda*). After 7 days, the effect in % is determined 100% means that all caterpillars have been killed; 0% means that none of the caterpillars have been killed.

In this test, for example, the following compounds of the Preparation Examples show, at an application rate of 100 g/ha, an effect of 83%:11

In this test, for example, the following compounds of the Preparation Examples show, at an application rate of 100 g/ha, an activity of 100%:

13, 14, 25, 26, 27, 30, 31, 32, 34, 35, 36, 37, 38, 39, 40, 41, 42, 43, 44

Example 2

Phaedon Test

PHAECO Spray Treatment

Solvents: 78.0 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amount of solvents and emulsifier, and the concentrate is diluted with emulsifier-containing water to the desired concentration. Discs of Chinese cabbage (*Brassica pekinensis*) are sprayed with an active compound preparation of the desired concentration and, after drying, populated with larvae of the mustard beetle (*Phaedon cochleariae*).

After 7 days, the activity in % is determined. 100% means that all beetle larvae have been killed; 0% means that none of the beetle larvae have been killed.

In this test, for example, the following compounds of the Preparation Examples show, at an application rate of 100 g/ha, an activity of 83%:11, 12

In this test, for example, the following compounds of the Preparation Examples show, at an application rate of 100 g/ha, an activity of 100%:

10, 13, 25, 26, 27, 30, 32, 34, 35, 36, 37, 38, 39, 40, 41, 42, 43, 44

Example 3

*Tetranychus* Test, OP-Resistant

TETRUR Spray Treatment

Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amount of solvents and emulsifier, and the concentrate is diluted with emulsifier-containing water to the desired concentration. Discs of bean leaves (*Phaseolus vulgaris*) which are infested by all stages of the greenhouse red spider mite (*Tetranychus urticae*) are sprayed with an active compound preparation of the desired concentration.

After 6 days, the activity in % is determined. 100% means that all of the spider mites have been killed; 0% means that none of the spider mites have been killed.

In this test, for example, the following compounds of the Preparation Examples show, at an application rate of 100 g/ha, an activity of 80%:8

In this test, for example, the following compounds of the Preparation Examples show, at an application rate of 100 g/ha, an activity of 100%:3

Example 4

*Myzus* Test

MYZUPE Spray Treatment

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amount of solvents and emulsifier, and the concentrate is diluted with emulsifier-containing water to the desired concentration.

Discs of Chinese cabbage (*Brassica pekinensis*) infested by all stages of the green peach aphid (*Myzus persicae*) are sprayed with an active compound preparation of the desired concentration.

After 6 days, the effect in % is determined. 100% means that all of the aphids have been killed; 0% means that none of the aphids have been killed.

In this test, for example, the following compounds of the Preparation Examples show, at an application rate of 100 g/ha, an activity of 80%:42

In this test, for example, the following compounds of the Preparation Examples show, at an application rate of 100 g/ha, an activity of 100%:43

Example 5

*Boophilus microplus* Test

BOOPMI Injection

Solvent: dimethyl sulphoxide

To produce a suitable preparation of active compound, 10 mg of active compound are mixed with 0.5 ml of solvent and the concentrate is diluted with solvent to the desired concentration. The active compound solution is injected into the abdomen (*Boophilus microplus*), and the animals are transferred into dishes and stored in a climate-controlled room. The activity is assessed by position of fertile eggs.

After 7 days, the effect in % is determined. 100% means that none of the ticks has laid any fertile eggs.

In this test, for example, the following compounds of the Preparation Examples show an activity of 100% at an application rate of 20 µg/animal: 34, 37, 38, 39, 40, 41.

In this test, for example, the following compounds of the Preparation Examples show an activity of 98% at an application rate of 20 µg/animal: 35

Example 6

*Musca domestica* Test

MUSCDO

Solvent: dimethyl sulphoxide

To produce a suitable preparation of active compound, 10 mg of active compound are mixed with 0.5 ml of dimethyl sulphoxide and the concentrate is diluted with water to the desired concentration. Vessels containing a sponge treated with the active compound preparation of the desired concentration are populated with adult *Musca domestica*.

After 2 days, the kill in % is determined. 100% means that all of the flies have been killed; 0% means that none of the flies have been killed.

In this test, for example, the following compounds of the Preparation Examples show an efficacy of 100% at an application rate of 100 ppm: 37

Example 7

*Lucilia cuprina* Test

LUCICU

Solvent: dimethyl sulphoxide

To produce a suitable preparation of active compound, 10 mg of active compound are mixed with 0.5 ml of dimethyl sulphoxide and the concentrate is diluted with water to the desired concentration. Vessels containing horse meat treated with the active compound preparation of the desired concentration are populated with about 20 *Lucilia cuprina* larvae.

After 2 days, the kill in % is determined. 100% means that all of the larvae have been killed; 0% means that none of the larvae have been killed.

In this test, for example, the following compounds of the Preparation Examples show an efficacy of 100% at an application rate of 100 ppm: 3, 34, 35, 37, 38, 39, 40, 41.

10. A compound according to claim 1, in which the compound has the following structure:
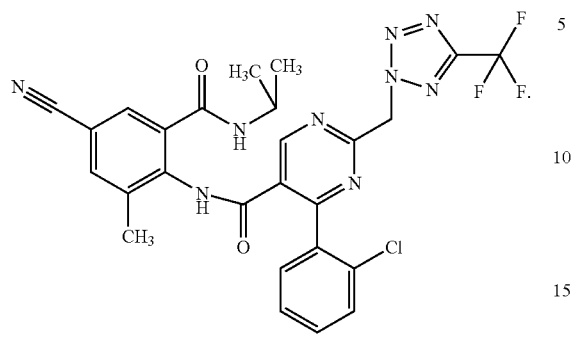

The invention claimed is:

1. An anthranilic acid derivative of formula (I)

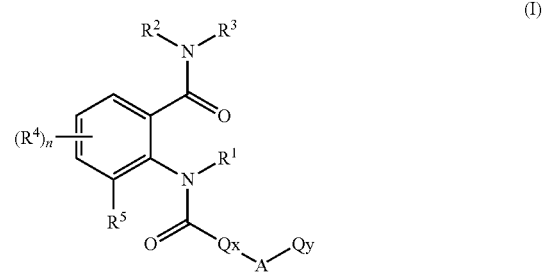

in which
$R^1$ represents hydrogen,
$R^2$ represents hydrogen, $R^3$ represents hydrogen, methyl, ethyl, n-propyl, isopropyl, n-butyl, isobutyl, sec-butyl, tert-butyl, cyclopropyl, cyclobutyl, cyanomethyl, 1-cyanoethyl, 2-cyanoethyl, 1-cyano-n-propyl, 2-cyano-n-propyl, 3-cyano-n-propyl, 1-cyanoisopropyl, 2-cyanoisopropyl, phenyl or pyridyl, $R^4$ represents hydrogen, methyl, trifluoromethyl, cyano, fluorine, chlorine, bromine, iodine or trifluoromethoxy or two adjacent radicals $R^4$ represent —$(CH_2)_4$— or —(CH=CH—)$_2$— n represents 0 to 3, $R^5$ represents methyl, fluorine, chlorine, bromine or iodine, $Q_X$ represents thiazole, oxazole, pyrrole, imidazole, triazole, pyrimidine, or phenyl, which is monosubstituted by the group $R^7$

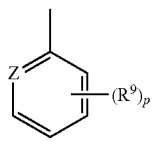

A represents —$CH_2$—, —$CH(CH_3)$, $C(CH_3)_2$, —$CH_2CH_2$—, —$CH(CN)$—, —$CH_2$—O— or —$C(=O)$—$CH_2$—, $Q_Y$ represents an optionally mono- or polysubstituted 5- or 6-membered heteroaromatic ring selected from the group consisting of Q-36 to Q-40, Q43, Q-58 to Q-59, Q62, Q63, an aromatic 9-membered fused heterobicyclic ring system Q-54 to Q-56 or a 5-membered heterocyclic ring Q-60 to Q-61 where the substituents independently of one another may be selected from the group consisting of $C_1$-$C_3$-alkyl, $C_1$-$C_3$-haloalkyl, $C_1$-$C_2$-alkoxy, halogen, cyano, hydroxyl, nitro and $C_1$-$C_2$-haloalkoxy or where the substituents independently of one another may be selected from the group consisting of phenyl and a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy, $C_1$-$C_4$-haloalkoxy, $R^9$ independently represents fluorine, chlorine or bromine P represents 1, Z represents N, CH, or CCl, and wherein the compound of formula (I) can furthermore comprise an N-oxide and/or salt thereof, wherein

Q-36

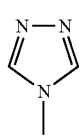

Q-37

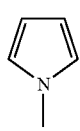

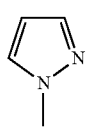

Q-38

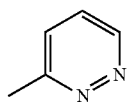

Q-39

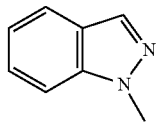

Q-40

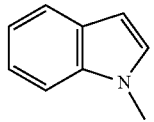

Q-43

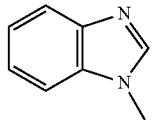

Q-54

Q-55

Q-56

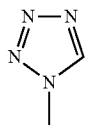

Q-58

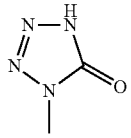

Q-59

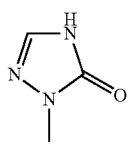

Q-60

Q-61

-continued

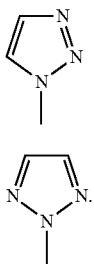
Q-62

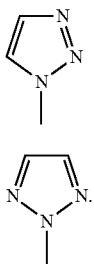
Q-63

2. A mixture of compounds according to claim 1, in which Qy is Q62 and Q63, the ratio of a compound of the formula (I) in which Qy is Q62 to a compound of the formula (I) in which Qy is Q63 being 60:40 to 99:1.

3. A mixture of compounds according to claim 1, in which Qy is Q58 and Q59, the ratio of a compound of the formula (I) in which Qy is Q58 to a compound of the formula (I) in which Qy is Q59 being 60:40 to 99:1.

4. A process for preparing a compound according to claim 1, comprising
(A) reacting an aniline of formula (II)

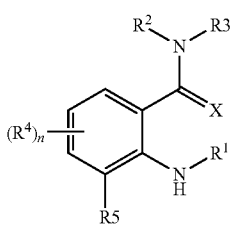
(II)

in which X represents O,
optionally, with a carbonyl chloride of formula (III)

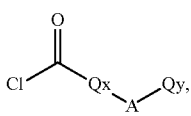
(III)

in the presence of an acid-binding agent; or
(B) reacting an aniline of formula (II)

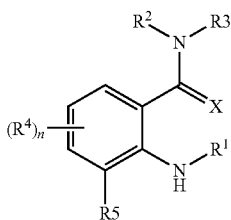
(II)

in which X represents O,
optionally, with a carboxylic acid of the formula (IV)

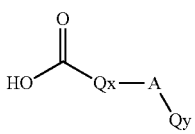
(IV)

in the presence of a condensing agent; or
(C) for the synthesis of an anthranilamide of formula (I) in which $R^1$ represents hydrogen,
optionally reacting a benzoxazinone of formula (V)

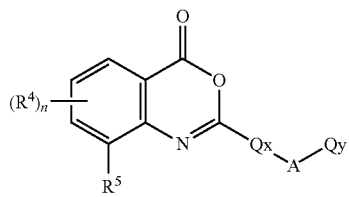
(V)

with an amine of the formula (VI)

(VI)

in the presence of a diluent.

5. A composition comprising at least one compound according to claim 1 and at least one salt of formula (XXIV)

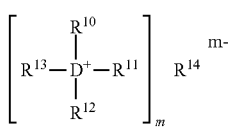
(XXIV)

in which
D represents nitrogen or phosphorus,
$R^{10}$, $R^{11}$, $R^{12}$, $R^{13}$, independently of one another represent hydrogen or in each case optionally substituted $C_1$-$C_8$-alkyl or mono- or polyunsaturated, optionally substituted $C_1$-$C_8$-alkylen where the substituents may be selected from the group consisting of halogen, nitro and, cyano,
m represents 1, 2, 3 or 4,
$R^{14}$ represents an inorganic or organic anion.

6. A composition comprising at least one compound according to claim 1 and at least one penetrant of formula (XXV)

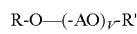  R-O—(-AO)$_V$-R'   (XXV)

in which
R represents straight-chain or branched alkyl having 4 to 20 carbon atoms
$R^1$ represents hydrogen, methyl, ethyl, n-propyl, isopropyl, n-butyl, isobutyl, tert-butyl, n-pentyl or n-hexyl,
AO represents an ethylene oxide radical, a propylene oxide radical, a butylene oxide radical or represents a mixture of ethylene oxide and propylene oxide radicals or butylene oxide radicals and
V represents a number from 2 to 30.

7. An agrochemical composition comprising at least one compound according to claim 1 and at least one extender and/or surfactant.

8. A process for producing an agrochemical composition comprising mixing at least one compound according to claim 1 with at least one extender and/or surfactant.

9. Method for controlling animal pests comprising applying at least one compound according to of claim 1 to animal pests and/or phytopathogenic fungi and/or their habitat and/or seed.